US006573387B1

(12) United States Patent
Sharpless et al.

(10) Patent No.: US 6,573,387 B1
(45) Date of Patent: Jun. 3, 2003

(54) SYNTHESIS OF α,β-SUBSTITUTED AMINO AMIDES, ESTERS, AND ACIDS

(75) Inventors: K. Barry Sharpless, La Jolla, CA (US); A. Erik Rubin, Plainsboro, NJ (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/381,407

(22) PCT Filed: Mar. 20, 1998

(86) PCT No.: PCT/US98/05654

§ 371 (c)(1),
(2), (4) Date: Jan. 31, 2000

(87) PCT Pub. No.: WO98/42657

PCT Pub. Date: Oct. 1, 1998

Related U.S. Application Data

(60) Provisional application No. 60/043,790, filed on Apr. 11, 1997, and provisional application No. 60/041,029, filed on Mar. 21, 1997.

(51) Int. Cl.$^7$ .................. C07D 203/04; C07C 233/05
(52) U.S. Cl. .................. 548/965; 544/176; 546/134; 546/136; 560/12; 562/553; 562/575; 564/164
(58) Field of Search .................. 548/965; 546/134, 546/136; 560/12; 562/575, 553; 564/164; 544/176

(56) References Cited

U.S. PATENT DOCUMENTS 5,859,281 A * 1/1999 Sharpless et al. ............. 560/12

OTHER PUBLICATIONS

Sharpless, et al., "Osmium–Catalyzed Vicinal Oxyamination of Olefins by Chloramine–T", *J. Org. Chem. 41:* 177–179 (1976).
Herranz, et al., "Improvements in the Osmium–Catalyzed Oxyamination of Olefins by Chloramine–T", *J. Org. Chem. 43:* 2544–2548 (1978).
Bennani, et al., "Asymmetric Dihydroxylation (AD) of N,N–Dialkyl and N–Methoxy–N–methyl α,β– and β,γ–Unsaturated Amides", *Tet. Lett. 34:* 2079–2082 (1993).
Evans, et al., "Bis(oxazoline)–Copper Complexes as Chiral Catalysts for the Enantioselective Aziridination of Olefins", *J. Am. Chem. Soc. 115:* 5328–5329 (1993).
Tanner, "Chiral Aziridines—Their Synthesis and Use in Stereoselective Transformations", *Angew. Chem. Int. Ed. Engl. 33:* 599–619 (1994).

Davis, et al., "Asymmetric Synthesis and Reactions of cis–N–(p–Toluenesulfinyl)aziridine–2–carboxylic Acids", *J. Org. Chem. 59:* 3243–3245 (1994).
Li, et al., "Catalytic Asymmetric Aminohydroxylation (AA) of Olefins", *Angew. Chem. Int. Ed. Engl. 35:* 451–454 (1996).
Shibasaki, et al., "Catalytic Asymmetric Carbon–Carbon Bond–Forming Reaction Utilizing Rare Earth Metal Complexes", *Pure. Appl. Chem. 68:* 523–530 (1996).
Larrow, et al., "Kinetic Resolution of Terminal Epoxides via Highly Regioselective and Enantioselective Ring Opening with TMSN$_3$. An Efficient, Catalytic Route to 1,2–Amino Alcohols", *J. Am. Chem. Soc. 118:* 7420–7421 (1996).
Rudolph, et al., "Smaller Substituents on Nitrogen Facilitate the Osmium–Catalyzed Asymmetric Aminohydroxylation", *Angew. Chem. Int. Ed. Engl. 35:* 2810–2813 (1996).
Li, et al., "N–Halocarbamate Salts Lead to More Efficient Catalytic Asymmetric Aminohydroxylation", *Angew. Chem. Int. Ed. Engl. 35:* 2813–2817 (1996).
Bruncko, et al., "N–Bromoacetamide—A New Nitrogen Source for the Catalytic Asymmetric Aminohydroxylation of Olefins", *Angew. Chem. Int. Ed. Engl. 36:* 1483–1486 (1997).
Maligres, et al., "Nosylaziridines: Activated Aziridine Electrophiles", *Tet. Lett. 38:* 5253–5256 (1997).
Sun, et al., "tert–Butylsulfonyl (Bus), a New Protecting Group for Amines", *J. Org. Chem. 62:* 8604–8608 (1997).
Osborn, et al., "The Asymmetric Synthesis of Aziridines", *Tetrahedron: Asymmetry 8:* 1693–1715 (1997).
Rubin, et al., "A Highly Efficient Aminohydroxylation Process", *Angew. Chem. Int. Ed. Engl. 36:* 2637–2640 (1997).

* cited by examiner

Primary Examiner—Shailendra Kumar
(74) Attorney, Agent, or Firm—Donald G. Lewis

(57) ABSTRACT

α,β-Unsaturated amides and esters are converted to α,β-substituted amino amides, esters, and acids. An α,βunsaturated amide or ester is first converted to an α,β-hydroxysulfonamide or hydroxycarbamate amide or ester using an osmium-catalyzed aminohydroxylation. The α,β-hydroxysulfonamide or hydroxycarbamate amides or esters is then cyclodehydrated to produce a α,β-N-sulfonyl- or the α,β-N-carbamoylaziridine amide or ester. The ring of aziridine intermediate is then nucleophilically opened in a regioselective manner with a variety of nucleophiles to give the $g(α,β$-substituted amino- amides or esters. Preferred nucleophiles include sulfur, oxygen, carbon, and nitrogen nucleophiles.

13 Claims, 31 Drawing Sheets

| Entry | Substrate | t [h] [b] | Regioisomeric ratio 2:3 [c] | Isolated yield of rac-2 [M.p. (°C)] [d] |
|---|---|---|---|---|
| 1 | Ph-CH=C(H)-C(O)-N(OMe)(Me)  1a | 1 | 7.3:1 | 82% [180-181] |
| 2 | Ph-CH=C(H)-C(O)-NMe₂  1b | 4 | 5.0:1 | 75% [176-177] |
| 3 | Ph-CH=C(H)-C(O)-N(i-Pr)₂  1c | 20 | 3.3:1 | 65% [223-225] |
| 4 | Ph-CH=C(H)-C(O)-NEt₂  1d | 6 | 2.8:1 | 65% [170-171] |
| 5 | Ph-CH=C(H)-C(O)-morpholine  1e | 2 | 2.6:1 | 51% [185-186] |
| 6 | Ph-CH=C(H)-C(O)-NH-t-Bu  1f | 2 | 1.6:1 | [e] |

| Entry | Substrate | Procedure [mol% Os] [a,b] | t [h] [c] | Regioisomeric ratio 2:3 [d] | Yield |
|---|---|---|---|---|---|
| 1 | 1a | A [0.10]* [e] | 4 | 6.5:1 | 93% |
| 2 | 1b | A [0.25] | 12 | 5.0:1 | 94% |
| 3 | 1b | A [0.20] [e] | 12 | 3.0:1 | 94% |
| 4 | 1g | A [0.25]* | 2.5 | 3.7:1 | 95% |
| 5 | 1h | A [0.50]* | 4 | 5.8:1 | 95% |
| 6 | 1i | B [0.50] | 10 | 10:1 | 99% |
| 7 | 1j | B [0.50] | 10 | 1:1.4 | 97% |
| 8 | 1k | B [1.0] | 23 | >20:1 [f] | 90% |
| 9 | 1l | B [0.50]* [g] | 24 | 3.0:1 | 99% |

FIG. 3

| Entry | Substrates (ratio) | Product | M.p. (°C) | Yield [a] |
|---|---|---|---|---|
| 1 | 2b/3b (5.0:1) | rac-4b | 130-131 | 95% |
| 2 | 2g/3g (3.7:1) | rac-4g | 50-53 | 97% |
| 3 | 2h/3h (5.8:1) | rac-4h | 127-128 | 94% |
| 4 | 2i/3i (10:1) | 4i | oil | 81% |
| 5 | 2j/3j (1:1.4) | rac-4j | 151-152 | 92% |
| 6 | 2l/3l (3.0:1) | rac-4l | oil | 87% |

| Compound (5':6') | NucH | Reaction Conditions[a] | Regioselectivity (C-2:C-3)[b] | Yield of major (%)[c] | M.p. of major (°C)[d] |
|---|---|---|---|---|---|
| 16 | butyl-SH | A | >98:2 | 76 | 178–179 |
| 17 | tert-butyl-SH | A | >98:2 | 89 | 231–232 |
| 18 | 4,6-dimethyl-2-mercaptopyridine | A | >98:2 | 84 | 195–196 |
| 19 | furfurylamine | B | 13:87 | 69 | 160–161 |
| 20 | piperidine | C | 10:90 | 71 | 175–176 |
| 21 | aniline | D | 10:90 | 65 | 155–156 |
| 22 | benzenesulfonamide | E | N/A | 80 | 217–218 |
| 23 | N-methyl-p-toluenesulfonamide | E | 96:4 | 74 | 208–209 |
| 24 | 4-methoxyphenol | F | 93:7 | 69 | 188–189 |
| 25 | phenol | F | 90:10 | 63 | 163–165 |

FIG. 7

X=NHSO₂R, Y=OH
or X=OH, Y=NHSO₂R

Nucleophiles: Thiols, Phenols, Azide, Sulfonamides, Amines

| Entry | Amine | Aziridine | Regioselectivity (C-2:C-3) | Yield (%)[d] |
|---|---|---|---|---|
| 1 | PhCH$_2$NH$_2$ | 4b[a] | 9:91 | 97 |
| 2 | furfurylamine | 4b[b] | 13:87 | 99 (69) |
| 3 | " | 4j[b] | 50:50 | 97 |
| 4 | piperidine | 4b[a] | 10:90 | 99 (71) |
| 5 | " | 4g[a] | 29:71 | 99 |
| 6 | " | 4j[b] | 30:70 | 99 |
| 7 | " | 4i[c] | 50:50 | 99 |
| 8 | PhNH$_2$ | 4b[c] | 10:90 | 99 (65) |

FIG. 17

| Entry | Phenol | Aziridine | Regioselectivity (C-2:C-3) | Yield (%)[b] |
|---|---|---|---|---|
| 1 | 4-nitrophenol (O$_2$N-C$_6$H$_4$-OH) | 4b | 75:25 | 87 (76) |
| 2 | 4-chlorophenol (Cl-C$_6$H$_4$-OH) | 4b | 90:10 | 93 (68) |
| 3 | " | 4j | 80:20 | 77 |
| 4 | phenol | 4b | 90:10 | 99 (63) |
| 5 | 4-methylphenol (Me-C$_6$H$_4$-OH) | 4b | 93:7 | 94 (73) |
| 6 | 4-methoxyphenol (MeO-C$_6$H$_4$-OH) | 4b | 93:7 | 90 (69) |

FIG. 18

| Entry | Sulfonamide | Aziridine | Regioselectivity (C-2:C-3) | Yield (%)[b] |
|---|---|---|---|---|
| 1 | benzyl-CH$_2$-SO$_2$NH$_2$ | 4b | 91:9 | 87 |
| 2 | 4-O$_2$N-C$_6$H$_4$-SO$_2$NH$_2$ | 4g | 95:5 | 95 |
| 3 | 4-Me-C$_6$H$_4$-SO$_2$NH$_2$ | 4b | - | 88 (80) |
| 4 | " | 4j | - | 97 |
| 5 | 4-Br-C$_6$H$_4$-SO$_2$NH$_2$ | 4b | 91:9 | 99 (75) |
| 6 | C$_6$H$_5$-SO$_2$NH$_2$ | 4b | 94:6 | 99 (78) |
| 7 | Me-SO$_2$NH$_2$ | 4b | 96:4 | 95 (74) |

FIG. 19

| Entry | Thiol | Aziridine | Regioselectivity (C-2:C-3) | Yield (%)[b] |
|---|---|---|---|---|
| 1 |  | 4b | >98:2 | 99 (89) |
| 2 | " | 4g | 95:5 | 99 |
| 3 | " | 4j | 95:5 | 99 |
| 4 | " | 4i | 95:5 | 89 |
| 5 |  | 4b | >98:2 | 99 (84) |

| Entry | Thiol | Aziridine | Regioselectivity (C-2:C-3) | Yield (%)[b] |
|---|---|---|---|---|
| 6 | PhCH₂SH (benzyl thiol) | 4b | >98:2 | 98 (95) |
| 7 | CH₃CH₂CH₂CH₂SH | 4b | >98:2 | 98 (76) |
| 8 | " | 4g | 95:5 | 97 |
| 9 | furfuryl-CH₂SH | 4b | >98:2 | 99 (79) |
| 10 | " | 4j | 98:2 | 95 |
| 11 | (CH₃)₃C-SH | 4b | >98:2 | 98 (89) |
| 12 | " | 4i | 95:5 | 89 |

FIG. 21

| Entry | Azide Source | Solvent | Additive (equivalents) | Regioselectivity (C-2:C-3) | Yield (%)[c] |
|---|---|---|---|---|---|
| 1 | NaN$_3$ | DMF[a] | - | 77:23 | 99 |
| 2 | NaN$_3$ | DMF[a] | NH$_4$Cl (1.5) | 77:23 | 99 |
| 3 | NaN$_3$ | MeOH[b] | - | 16:84 | 99 |
| 4 | NaN$_3$ | MeOH[b] | MgSO$_4$ (0.55) | 22:78 | 98 |
| 5 | TMSN$_3$ | PhMe[a] | ZnCl$_2$ (0.05) | 5:95 | 98 (77) |

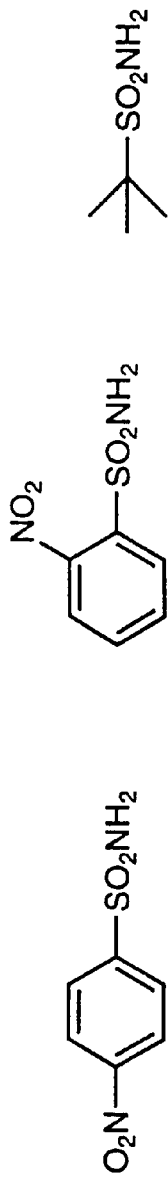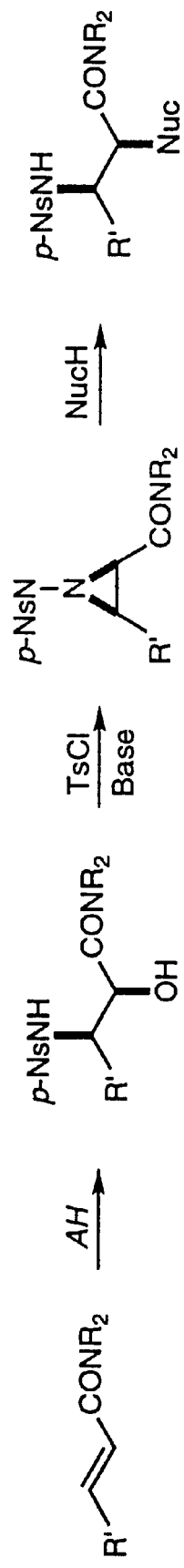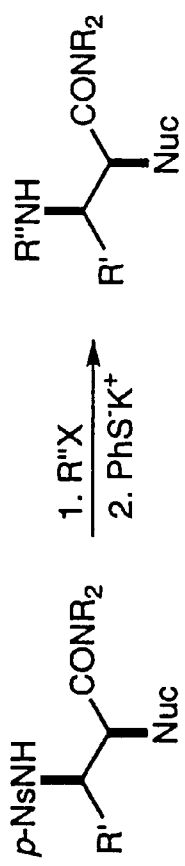
FIG. 23A
FIG. 23B

| Entry | Substrate | Regioisomeric ratio β:α | Yield |
|---|---|---|---|
| 1 | PhCH=CH-C(O)-N(Me)(OMe) | 3.3:1 | 93% |
| 2 | CH2=CH-C(O)-NMe2 | >20:1 | 84% |
| 3 | CH3CH2CH2-CH=CH-C(O)-NMe2 | 2.5:1 | 91% |
| 4 | CH2=C(Me)-C(O)-NEt2 | >20:1 | 90% |
| 5 | (2,6-diMe-C6H3)-CH=CH-C(O)-NMe2 | 4.5:1 | 82% |
| 6 | (3-O2N-C6H4)-CH=CH-C(O)-NMe2 | 1.5:1 | 94% |
| 7 | (4-MeO-C6H4)-CH=CH-C(O)-morpholine | 5.0:1 | 65% |
| 8 | (4-Br-C6H4)-CH=CH-C(O)-N(Me)(OMe) | 1.8:1 | 81% |
| 9 | (4-Me-C6H4)-CH=CH-C(O)-morpholine | 2.7:1 | 84% |
| 10 | PhCH=CH-C(O)-NH-iPr | 2.3:1 | 71% |

FIG. 33

SYNTHESIS OF α,β-SUBSTITUTED AMINO AMIDES, ESTERS, AND ACIDS

DESCRIPTION

This application is a 371 of PCT/US98/05654 filed Mar. 20, 1998, which claims the benefit of provisional applications 60/043,790 filed Apr. 11, 1997 and 60/041,029 filed Mar. 21, 1997.

This invention was made with government support under Contract No. GM 28384 by the National Institutes of Health and Contract No. CHE-9531152 by the National Science Foundation. The government has certain rights in the invention.

FIELD OF THE INVENTION

The invention relates to the conversion of α,β-unsaturated amides and esters to α,β-substituted amino amides, esters, and acids. More particularly, the invention relates to three-step converion processes employing an osmium-catalyzed aminohydroxylation step to produce α,β-hydroxysulfonamide or hydroxycarbamate amide or ester intermediates, a cyclodehydration step to produce an α,β-N-sulfonyl- or the α,β-N-carbamoylaziridine amides or esters and a regioselective nucleophilically induced ring-opening step to give the α,β-substituted amino- amides or esters.

SUMMARY

One aspect of the invention is directed to a method for converting an α,β-unsaturated substrate to a blocked or unblocked α,β-substituted amino product. The α,β-unsaturated substrate may be an α,β-unsaturated amide or an α,β-unsaturated ester. The α,β-substituted amino product corresponds to the α,β-unsaturated substrate, i.e., it is an α,β-substituted amino amide or α,β-substituted amino ester. The α,β-substituted amino product may be either blocked or unblocked. The blocked α,β-substituted amino product includes a blocked amino group. The unblocked α,β-substituted amino product includes an unblocked amino group.

In the first step of the conversion, the α,β-unsaturated substrate is oxidized with a nitrogen source for making a racemic mixture of an α,β-hydroxy-amino intermediate. The α,β-hydroxy-amino intermediate includes a blocked amino group and corresponds to the substrate, i.e., it is an α,β-hydroxy-amino amide or an α,β-hydroxy-amino ester. Preferred nitrogen sources include carbamate and sulfonamide. In a preferred mode, the oxidation is a regioselective osmium-catalyzed aminohydroxylation. Then, the above α,β-hydroxy-amino intermediate is cyclodehydrated for producing an α,β-N-blocked-aziridine intermediate having an aziridine ring, the α,β-N-blocked-aziridine intermediate. The aziridne intermediate corresponds to the starting material, i.e., it is an α,β-N-blocked-aziridine amide or an α,β-N-blocked-aziridine ester. Then, the aziridine ring of the α,β-N-blocked-aziridine intermediate is opened with a nucleophile in a regioselective manner for making the blocked α,β-substituted amino product. Preferred nucleophiles are hydrocarbons having a nucleophilic moiety selected from a group consisting of thiol, alcohol, nitrile and amine. Finally, the amino group of the blocked α,β-substituted amino product is optionally unblocked to produce the unblocked α,β-substituted amino product. The amide or ester group of the blocked or unblocked α,β-substituted amino product may be hydrolyzed for forming a blocked or unblocked α-substituted β-amino acid.

Another aspect of the invention is directed to the synthesis of a library comprising a plurality of compounds using the above described method.

Another aspect of the invention is directed to a method for converting an α-β unsaturated substrate to a racemic mixture of an α-hydroxy-β-amino regio-isomer product having a blocked amino group. The α-β unsaturated substrate may be an α-β unsaturated amide or an α-β unsaturated ester. The α-hydroxy-β-amino regio-isomer product is formed by admixing a nitrogen source and a hydroxyl radical with the α-β unsaturated substrate. The method is of a type which employs a reaction solution which includes osmium as a catalyst, The α-β unsaturated amide substrate is present and soluble at a stoichiometric concentration within the reaction solution. The osmium is present and soluble within the reaction solution at a catalytic concentration. Preferred nitrogen source include sulfonamide and carbamate.

Another aspect of the invention is directed to a method for converting an α-β unsaturated substrate to an asymmetric α-hydroxy-β-amino regio-isomer product having a blocked amino group. The α-β unsaturated substrate may be an α-β unsaturated amide or an α-β unsaturated ester. The asymmetric αhydroxy-β-amino regio-isomer product is formed by admixing a nitrogen source, a chiral ligand, and a hydroxyl radical with the α-β unsaturated substrate. The method employs a reaction solution which includes osmium as a catalyst. The α-β unsaturated substrate is present and soluble at a stoichiometric concentration within the reaction solution. The osmium is present and soluble within the reaction solution at a catalytic concentration. Preferred nitrogen sources include sulfonamide and carbamate. The chiral ligand is selected for enantiomerically directing the addition of the nitrogen source and hydroxyl radical. In a preferred mode, the admixture occurs in a co-solvent mixture containing an organic component and an aqueous component.

Another aspect of the invention is directed to a method for converting an α,β-hydroxy-amino substrate having a blocked amino group to an α,β-N-blocked-aziridine product. The α,β-hydroxy-amino substrate may be an α,β-hydroxy-amino amide or an α,β-hydroxy-amino ester. The hydroxyl moiety of the α,β-hydroxy-amino substrate is activated with an activating agent for producing an activated α,β-hydroxy-amino intermediate having an activated hydroxyl moiety and an amino nitrogen. The activated α,β-hydroxy-amino intermediate corresponds to the substrate and may be an activated α,β-hydroxy-amino amide or an activated α,β-hydroxy-amino ester. Then, the activated hydroxyl moiety of the activated α,β-hydroxy-amino intermediate is displaced with the amino nitrogen by base promoted ring closure for forming the α,β-N-blocked-aziridine product.

BRIEF DESCRIPTION OF FIGURES

FIG. 3 illustrates the aminohydroxylation of various α,β-unsaturated amides with the following footnotes: [a] See experimental procedure. [b] An asterisk indicates that $OsO_4$ (as a 0.1 M solution in MeCN) was used in place of $K_2OsO_2(OH)_4$. [c] Approximate reaction time required for the disappearance of the starting olefin as determined by TLC. [d] Determined by $^1H$ NMR. [e] The olefin concentration was 0.8 M. [f] The presence of 3k was not detected by $^1H$ NMR. [g] tBuOH was used as the cosolvent.

FIG. 7 shows a table with yields and regioselectivities for the addition of various nucleophiles to rac-4b with the following footnotes: a) A: 1.2 equiv. NucH, 1.2 equiv. $K_2CO_3$, DMF (0.5 M), RT; B: 1.2 equiv. NucH, n-PrOH (1.0 M), 80° C.; C: ca. 5 equiv. NucH, 100° C.; D: 1.2 equiv. NucH, DMF (1.0 M), 80° C.; E: 1.0 equiv. NucH, 1.0 equiv. $K_2CO_3$, DMF (0.5 M), 100° C.; F: 1.2 equiv. NucH, 1.2 equiv. $K_2CO_3$, DMF (1.0 M), 80° C.; b) (C-2:C-3) refers to the ratio of the addition product at the position α to the carbonyl to that at the position β to the carbonyl (determined by integration of the 1H NMR spectra of the crude reaction mixtures); c) yields of the pure major regioisomers after a single recrystallization from i-PrOH (compounds 16–19, 21–24), or EtOAc-hexanes (compounds 20, and 25); d) Melting points of the pure major regioisomers.

FIG. 4) with nucleophiles undergo highly regioselective ring opening. The following conditions are reported: NucH= ArSH or RSH: 1–2 equiv NucH, 1–2 equiv $K_2CO_3$, DMF, RT, NucH=ArOH or $ArSO_2NH_2$: 1–3 equiv NucH, 1–3 equiv $K_2CO_3$, DMF, 100° C. NucH=$R_2NH$, $ArNH_2$, or $RNH_2$: ca. 10 equiv NucH (neat), 100° C.

FIG. 17 illustrates various reactions run with compounds 4b, 4g, 4j and 4i with amine nucleophiles using the following conditions: a) Reaction was run in neat amine (ca. 10 equiv.), 80° C.; b) Reaction was run in n-PrOH (1 M), 80° C.; c) Reaction was run in DMF (1 M), 80° C.; d) Recrystalized yields in parentheses.

FIG. 18 illustrates various reactions run with compounds 4b, 4g, 4j and 4i with phenol nucleophiles using the following conditions: a) 1.2 equiv. phenol, 1.2 equiv $K_2CO_3$ DMF (1 M), 80° C.; b) Recrystalized yields in parentheses.

FIG. 19 illustrates various reactions run with compounds 4b, 4g, 4j and 4i with sulfonamide nucleophiles using the following conditions:a) 1 equiv. sulfonamide, 1 equiv $K_2CO_3$, DMF (0.5–1 M), 80–100° C.; b) Recrystalized yields in parentheses.

FIG. 21 illustrates various reactions run with compounds 4b, 4g, 4j and 4i with thiol nucleophiles using the following conditions: a) 1.2 equiv. thiol, 1.2 equiv $K_2CO_3$, DMF (0.5 M), RT; b) Recrystalized yields in parentheses.

FIG. 23 illustrates a) alternate sulfonamide oxidants; b) the use of these alternate sulfonamide oxidants for facile nitrogen deprotection.

FIG. 33 tabulates the aminohydroxylation of unsaturated amides with BusNClNa.

DETAILED DESCRIPTION OF THE INVENTION

The invention is directed to the conversion of α,β-unsaturated amides and esters to α,β-substituted amino amides, esters, and acids. The method being of a type which comprises three or four chemical steps consisting of:

Step 1. The conversion of an α,β-unsaturated amide or ester to an α,β-hydroxysulfonamide or hydroxycarbamate amide or ester using an osmium-catalyzed aminohydroxylation.

Step 2. Cyclodehydration of the α,β-hydroxysulfonamide or hydroxycarbamate amides or esters to produce the α,β-N-sulfonyl-or the α,β-N-carbamoylaziridine amides or esters.

Step 3. Regioselective nucleophilic ring-opening of the α,β-N-sulfonyl- or the α,β-N-carbamoylaziridine amides or esters with a variety of nucleophiles-including sulfur, oxygen, carbon, and nitrogen nucleophiles-to give the α,β-substituted amino- amides or esters.

Step 4 (optional). Acid-catalyzed hydrolysis of the α,β-substituted amino amides or esters to produce the α,β-substituted amino acids.

EXAMPLE 1

A Highly Efficient Aminohydroxylation Process

To further develop the AA and to expand its scope, α,β-unsaturated amides were examined as a potential substrate class and gave only racemic products in the p-toluenesulfonamide-based AA. The absence of asymmetric induction in the AA of tertiary α,β-unsaturated amides is particularly surprising since these olefins are excellent substrates for the AD. (See Y. L. Bennani, K. B. Sharpless, Tetrahedron Lett. 1993, 34, 2079–2082.)

Figures 1, 2:
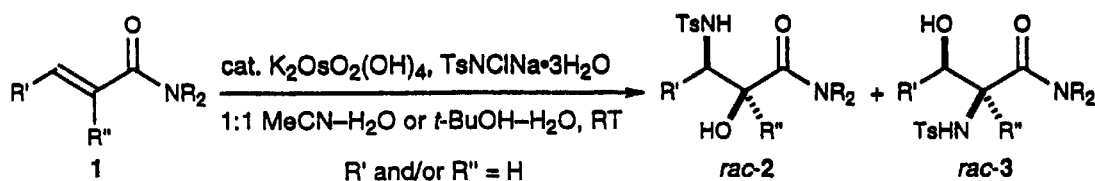
FIG. 1 illustrates the p-Toluenesulfonamide-based aminohydroxylation of α,β-unsaturated amides.
FIG. 2 illustrates the effect of substrate N-substituents on the aminohydroxylation of cinnamamides with the following footnotes: [a] Reaction conditions: 1.0 mol % $K_2OsO_2(OH)_4$, 1.2 equiv $TsNClNa \cdot 3H_2O$, 1:1 MeCN—$H_2O$, RT, 0.2 M olefin. [b] Approximate reaction time required for the disappearance of the starting olefin as determined by TLC. [c] Determined by $^1H$ NMR. [d] Yield and melting point of the pure major regioisomer (2) after recrystallization of the crude product (which consisted of 2, 3, and excess $TsNH_2$) from iPrOH. [e] Recrystallization from iPrOH afforded a 72% yield of 2f and 3f in a 2:1 ratio, respectively.

On the other hand, α,β-unsaturated amides exhibited excellent reactivity and afforded very high yields of the hydroxysulfonamide products, whether or not ligand was added. A detailed characterization of the "ligand independent" aminohydroxylation of α,β-unsaturated amides is shown in FIG. 1.

The aminohydroxylation of different N-substituted cinnamamides (1a–1f; FIG. 2) gave excellent results even though much less of the osmate catalyst, chloramine salt, and solvent were employed than are optimal for the standard AA process (FIG. 2).

The standard conditions for the AA are: 4 mol % $K_2OsO_2(OH)_4$, 5 mol % alkaloid ligand, 3 equiv chloramine salt, 0.07 M olefin in 1:1 MeCN—$H_2O$ or 1:1 nPrOH—$H_2O$. The acetamide-based AA uses the same standard conditions but with 1.1 equivalents of AcNLiBr in place of the chloramine salt.

In all cases, the major regioisomer obtained was 2, in which the newly added nitrogen was in the benzylic position. A sample of the pure major product from the aminohydroxylation of N,N-dimethylcinnamamide (1b) was converted to its methyl ester analogue [step 1) 3N HCl(aq), 93%; step 2) 2.2 equiv TMSCl, MeOH, RT, 91% (see M. A. Brook, T. H. Chan, Synthesis 1983, 201–203)] and shown to be identical ($^1H$ and $^{13}C$ NMR) to an authentic sample of methyl-(R*,S*)-2-hydroxy-3-phenyl-3-(p-toluene-sulfonamido)propanoate. (See FIG. 1).

The above result is the same, albeit weaker, regioselectivity observed for cinnamate esters in the AA. However, under otherwise identical experimental conditions, the nature of the substituents on the amide nitrogen had a significant effect on the extent to which 2 was predominant over 3 as well as on the reaction rates. The Weinreb methoxymethyl cinnamamide (1a) proved to be the best substrate, giving the highest regioselectivity and requiring the shortest reaction time. However, indicating that rapid turnover and high regioselectivity are not necessarily directly related, N-t-butylcinnamamide (1f) was almost as reactive as 1a, yet gave the poorest regioselectivity of the cinnamamides examined.

Further studies with cinnamamide 1b (FIG. 2) demonstrated that higher initial olefin concentrations as well as much lower catalyst loadings could be employed without compromising either the yield or the regioselectivity of the aminohydroxylation. The regioselectivities observed for the aminohydroxylation of olefins 1a, 1b, and 1i–1k under the conditions of procedures A and B (FIG. 3) were the same as those observed for these same substrates under the conditions described in FIG. 2. In one case, however, when the concentration of 1b was raised from 0.5 M to 0.8 M and the catalyst load was decreased from 0.25 mol % to 0.20 mol %, a slight deterioration of the regioselectivity from 5.0:1 to 3.0:1 was observed (cf. FIG. 3, entries 2 and 3).

In addition, at olefin concentrations of 0.5 M or greater and with tBuOH in place of MeCN as the cosolvent, the hydroxysulfonamide products derived from cinnamamides precipitated directly from the reaction solution in high yield and could be conveniently isolated by filtration. This led to the development of two procedures for the aminohydroxylation of α,β-unsaturated amides: method A when the products are insoluble in the reaction mixture and method B when they are soluble. These procedures differ only in that the former calls for a 25% excess of the chloramine salt and tBuOH as the cosolvent, whereas the latter uses one equivalent of the cooxidant and MeCN as the cosolvent. The excess Chloramine-T in procedure A supports better turnover near the end of the reaction. However, the elimination of the necessity to remove excess p-toluenesulfonamide (produced in the reductive workup) from the product far outweighs the inconvenience of the slightly longer reaction times needed in procedure B because no excess chloramine salt is used. FIG. 3 lists results from the aminohydroxylation of different cinnamamides, alkyl-substituted acrylamides, and a parent acrylamide (1i) using procedures A and B.

As can be seen in FIG. 3, excellent yields of the hydroxysulfonamide products were obtained from each of the olefins examined. Most importantly, these high yields and short reaction times were achieved at high substrate concentrations, and at room temperature with as little as 0.10 mol % of the catalyst. In the old Chloramine-T-based racemic aminohydroxylation of olefins, 1 mol % $OsO_4$, reaction times in excess of 12 h, and temperatures of 60° C. were required to obtain moderate to good yields of the hydroxysulfonamide products. The poor turnover rates in the old system are now largely attributed to the small amount of water present in the original recipes. However, as mentioned earlier, in the absence of ligands the presence of more water does lead to greater intrusion of the competing dihydroxylation cycle. With olefins other than $\alpha,\beta$-unsaturated amides, diol can be expected to constitute up to 70% of the product mixture in some cases (H.-T. Chang, Ph.D. thesis, The Scripps Research Institute (USA), 1996).

It is the unique ability of $\alpha,\beta$-unsaturated amides (e.g., 1a–1k) to benefit from the rapid turnover rates associated with high water concentration while somehow also avoiding the paths leading to diol by-product, which accounts for their unprecedented efficiency in the aminohydroxylation process.

Figures 4, 5:
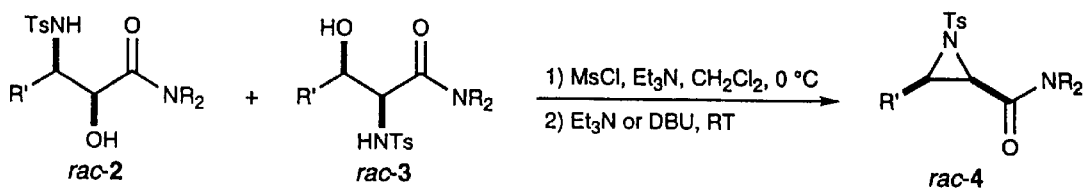
FIG. 4 illustrates the conversion of both regioisomeric aminohydroxylation products to the same aziridine.
FIG. 5 illustrates the preparation of aziridines from regioisomeric mixtures of hydroxysulfonamides 2 and 3 with the following footnote: [a] Yield of the pure aziridine after flash chromatography.

The hydroxysulfonamide products are generally highly crystalline, and the regioselectivity of the aminohydroxylation reaction is such that the major regioisomer is usually obtained in pure form following a single recrystallization of the isomeric mixture. However, for cases in which separation is difficult or in order to fully exploit the high combined yields in which the products are obtained, reactions which transform both regioisomers into the same product are of interest. One such example is cyclodehydration of the hydroxysulfonamides to give the corresponding aziridines (FIG. 4). So-called "activated aziridines" such as 4 are versatile synthetic intermediates and have found wide use in the synthesis of biologically active compounds (a) Tanner, Angew. Chem. 1994, 106, 625; Angew. Chem., Int. Ed. Engl. 1994, 33, 599–619; Pearson et al. in Comprehensive Heterocyclic Chemistry II, Vol. 1A (Ed.: A. Padwa), Pergamon, New York, 1996, pp. 1–60; Osborn et al. Tetrahedron: Asymmetry 1997, 8, 1693–1715).

The crude mixtures of hydroxysulfonamides 2 and 3, obtained directly from the aminohydroxylation of olefins 1, were cyclized to the aziridines 4 in a one-pot procedure (FIG. 4). The yields of the ring-closure for several pairs of regioisomers are listed in FIG. 5. Thus, a highly efficient two-step synthesis of azitidines 4 from readily available olefins and without the need for any purification of the intermediates is presented.

In conclusion, example 1 discloses that $\alpha,\beta$-unsaturated amides represent one of the few olefin classes for which the osmium-catalyzed aminohydroxylation reaction is highly efficient in the absence of added ligands. The method's principal advantages are excellent chemical yields, rapid turnover rates (enabling the use of very low catalyst loads), the ability to use high substrate concentrations, and the necessity for only one equivalent or a small excess of chloramine salt. The latter consideration along with the favorable "crystallinity factor" greatly simplifies product isolation and makes these processes ideal for large scale applications. In addition, the rapid emergence of diversity chemistry (Balkenhohl et al. Angew. Chem. 1996, 108, 2436–1487; Angew. Chem., Int. Ed. Engl. 1996, 35, 2288–2337) makes such powerful transformations, especially those yielding racemates, more important than ever. Another advantage of racemates, is that modern preparative chiral HPLC often enables access to both enantiomers. The pharmaceutical industry now favors this approach for quick "enantio-deconvolutiuon" of biological activity.

EXAMPLE 2

Diversity Chemistry Through the Regioselective Ring-opening of an Aziridine

The ring-opening of (2R*,3R*)-2-(N,N-dimethylcarbamoyl)-3-phenyl-1-(p-toluenesulfonyl) aziridine (4b) with heteroatom-based nucleophiles proceeds in high yields and with high and predictable regioselectivities. Ten examples are given and a new synthetic strategy for the generation of solution-phase libraries of amino acid derivatives is presented.

It is estimated that 1062–1063 reasonable organic compounds can be assembled from 30 atoms taken from C, H, N, O, P, S, and X (halogens; Bohacek et al. Med. Res. Rev. 1996;16:3–50). With these narrow criteria generating such an enormous set of possible structures, it is not surprising that the pharmaceutical industry has turned to the generation combinatorial chemical libraries to accelerate the small-molecule (MW<700) drug discovery process. Because there isn't enough mass in the universe to make even a single copy of every small-molecule drug candidate, directed combinatorial chemistry strategies have become the primary focus. However, it has been noted that as new macromolecular drug targets are discovered, there will be a need for the identification of new pharmacophores. It is possible that broad-based approaches to the generation of chemical libraries will become increasingly important in this respect. In either case, the onset of high throughput synthesis technology, especially in the solution-phase, has created a demand for robust and reliable chemical transformations which enable the introduction of diversity into chemical libraries through the combination of well-known pharmacophores onto new molecular scaffolds or through the elaboration of novel core structures.

To this end, our strategy is to use the Sharpless epoxidation, dihydroxylation, and amino hydroxylation methodologies for the oxidation of olefins to generate reactive intermediates which can be "clicked" together with a wide variety of building blocks via carbon-heteroatom linkages. In this respect, the ring-opening of the saturated three-membered heterocycles-e.g., epoxides and aziridines (Pearson et al. Aziridines and Azirines: Monocyclic. In: Padwa A, editor. Comprehensive Heterocyclic Chemistry II, Vol 1A. New York: Pergamon, 1996:1–60; Maligres et al. Tetrahedron Lett. 1997;38:5253–5256) retains its status as a key method for the construction of the 1,2-diheteroatom moiety, a common feature in drug-like molecules.

Figure 6:
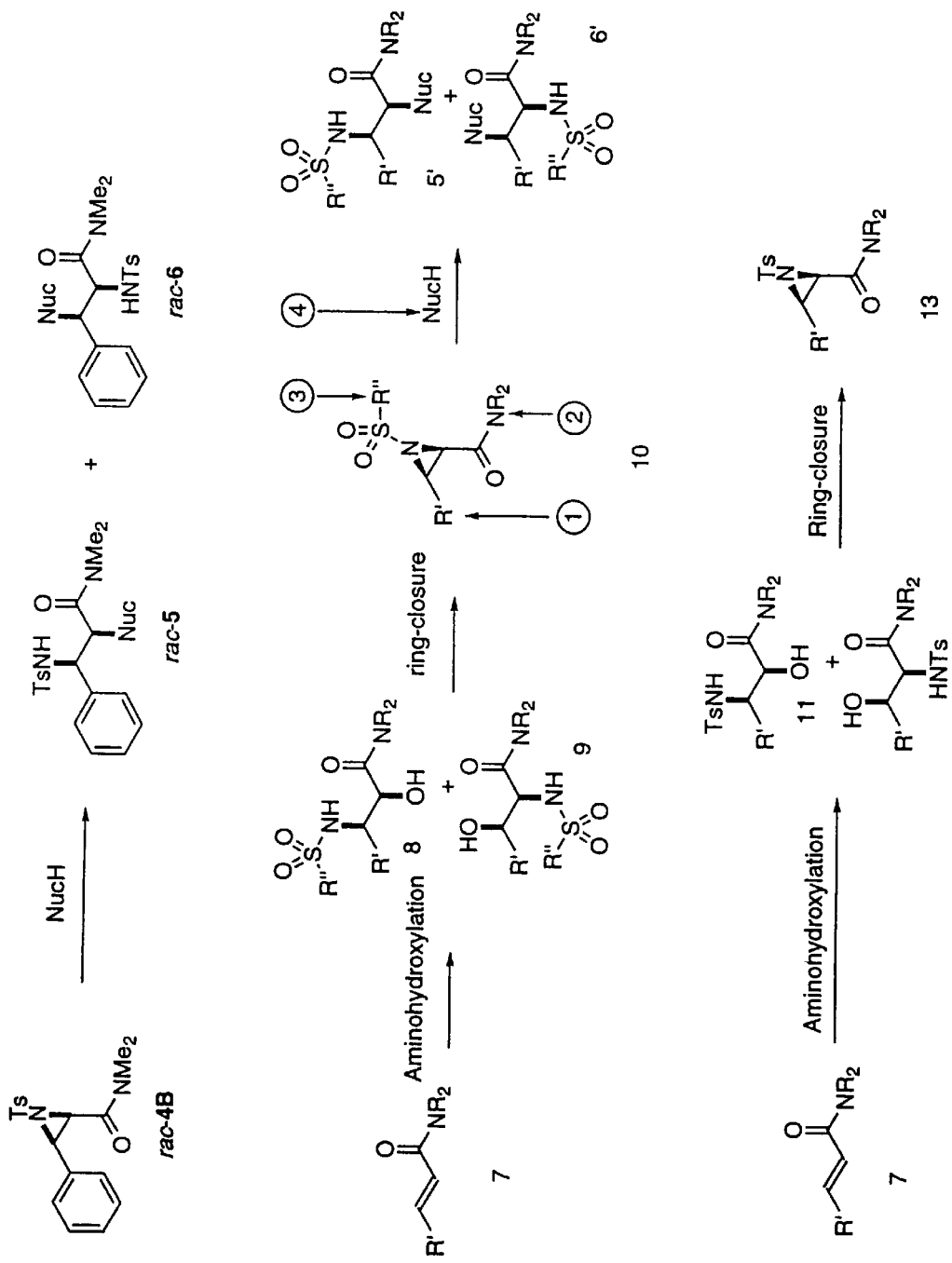
FIG. 6 illustrates the conversion of α,β unsaturated amides to racemic mixtures of hydroxysulfonamides which are then converted to azridines and then selectively opened with a nucleophile.

Example 1 (above) discloses a simple and expedient preparation of N-tosylaziridine-2-carboxamides via an especially efficient osmium-catalyzed aminohydroxylation of $\alpha,\beta$-unsaturated amides (see FIG. 6; middle transition). In this example, it is disclosed that the addition of a variety of heteroatom-based nucleophiles to one of these aziridines (4b) proceeds in a regioselective and predictable fashion, providing a novel synthetic route to solution-phase libraries of amino acid derivatives (FIG. 6; top transition).

FIG. 7 lists the results from the ring-opening of 4b with 10 nucleophiles. In each case the preference for addition at either the C-2 or the C-3 position of 4b was at least 87:13 (see compound 19) and in the case of the thiolate nucleophiles (compounds 16–18), the C-3 isomer was not detected by proton NMR spectroscopy of the crude reaction mixture.

The trends observed for the regiochemical preferences were as follows: neutral amine nucleophiles (compounds 19–21) were C-3 selective and anionic nucleophiles (compounds 16–18, compounds 22–25) were C-2 selective. Even the rather non-nucleophilic aniline (compound 21) was successful in this sequence but did suffer from a significantly longer reaction time (ca. 2 days compared to 10–15 h for the other additions). In addition to compounds 22 and 23, other aromatic sulfonamides such as bezenesulfonamide, p-bromobezenesulfonamide, and o- and p-nitrobezenesulfonamide successfully opened 4b with high C-2:C-3 selectivity (91:9–95:5) but failed to give pure compounds upon crystallization from i-PrOH or EtOAc-hexanes. In this series, the nitrobezenesulfonamide adducts are of particular interest due to their ability to be selectively alkylated and the ease with which they are deprotected.

The reaction conditions varied depending on the nature of the nucleophile and are described in the description of Figures for FIG. 7. The salient features are as follows: (a) the reactions are run at high concentrations (0.50–1.0 M in aziridine) which makes them adaptable to large scale applications, (b) The work-up is simple-typically, partitioning between EtOAc or methylene chloride and water followed by drying and evaporation of the organic phase, (c) the crude yields of the isomeric product mixtures (containing only the C-2 and C-3 adducts, or, in the case of the thiolate nucleophiles, only the C-2 adduct) were quantitative (98–100%), and (d) analytically pure products were typically obtained following a single recrystallyzation of the crude products or product mixtures from i-PrOH or EtOAc-hexanes.

With volatile amine nucleophiles such as piperidine (compound 20; FIG. 7), the opening reaction could be run in neat amine (5 equiv., ca. 2 M) at 100° C. for ca. 12 h. In this case, simple evaporation of the reaction mixture afforded the pure mixture of regioisomers in quantitative yield. A single recrystallization of this mixture from EtOAc-hexanes (ca. 2:1) afforded the pure C-3 adduct in 71% yield. Finally, in a brief study of the solvent effects on the regiochemistry of the addition of piperidine to 4b, n-PrOH or "no solvent" (vide supra) gave the same results (10:90, C-2:C-3), while in DMF the ratio dropped to 19:81, C-2:C-3.

In this example, regioselective nucleophilic ring-openings of aziridines derived from the aminohydroxylation of unsaturated amides are disclosed. When coupled together, these methods provide a simple and efficient pathway for the production of solution-phase libraries of amino acid derivatives. Especially important is that this sequence has all of the attributes required of a protocol suitable for automation. In addition, from beginning to end, this sequence offers four points of variability for the construction of combinatorial libraries-two from the α,β-unsaturated amide, one from the nitrogen source employed in the aminohydroxylation (FIG. 6; middle and bottom transitions), and one from the nucleophile used in the aziridine opening step (FIG. 6; top transition). This work represents the expansion along a single axis of this four-dimensional protocol. Robotics and automation can be employed to elaborate along all four axes.

EXAMPLE 3

Formation of Aziridines from α,β Unsaturated Amides

This example covers the conversion of α-β unsaturated amide substrates to tosylaziridine products. The method being of a type which employs a first reaction solution which includes osmium as a catalyst, the α-β unsaturated amide substrate being present and soluble at a stoichiometric concentration within the reaction solution, the osmium being present and soluble within the reaction solution at a catalytic concentration wherein said addition is performed using a nitrogen source selected from the group consisting of sulfonamide and carbamate for forming an α-β hydroxysulfonamide or α-β hydroxycarbamate amide product. Next, after purification, using a two-step one-pot procedure consisting of mesylation followed by base promoted ring closure, cyclodehydration of the α-β hydroxysulfonamide or α-β hydroxycarbamate amide product to form the aziridine is achieved.

More particularly, there are two aspects to this example:
1.) A method for forming an α-β hydroxysulfonamide or α-β hydroxycarbamate amide product using a osmium catalyzed aminohydroxylation from α-β unsaturated amides.
2.) A method for forming an α-β-N-tosylaziridine amide product from the α-β hydroxysulfonamide amide product as described in aspect 1 of the invention.

The osmium-catalyzed aminohydroxylation of α-β-unsaturated amides is a highly efficient process by which racemic N-protected β-aminoalcohols are obtained stereospecifically in excellent yields and with moderate to good regioselectivities (FIG. 1). With Chloramine-T (TsNClNa) as the nitrogen source, the reaction is most practical for cinnamamides and 3-alkyl acrylamides (FIGS. 2 and 3).

The high yields in which the aminohydroxylated products were obtained and the synthetic potential of the β-hydroxyamine and carboxamide units present in the products prompted us to explore further transformations of the regioisomeric hydroxysulfonamides 2 and 3 (FIG. 1).

Next, cyclodehydration of the mixture of regioisomeric hydroxysulfonamides to give N-tosylaziridines is performed. This is accomplished in excellent yields using a two-step one-pot procedure consisting of mesylation followed by base promoted ring closure (FIG. 4).

The aziridine rings can then be nucleophilically opened as described in example 4. Asymmetric aminohydroxylation (AA) reaction provides an easy route to enantiopure aminoalcohols. When applied to α-β-unsaturated esters, the AA can serve as a starting point for the enantiomeric deconvolution of the racemic components of the libraries.

EXAMPLE 4

Figure 8:
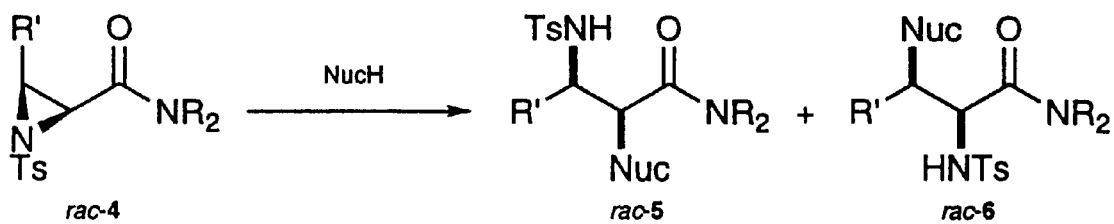
FIG. 8 illustrates the regioselective nucleophilic ring-opening of N-tosylaziridine-2-carboxamides (aziridines 4.

Conversion of Aziridines Formed from α,β-unsaturated Amides and Esters to α,β-substituted Amino Amides, Esters and Acids Studies on the reactivity of aziridines 4 (FIG. 4) with nucleophiles indicate that they undergo highly regioselective ring opening with a variety of sulfur, oxygen, and nitrogen-based nucleophiles (FIG. 8).

Figure 9:
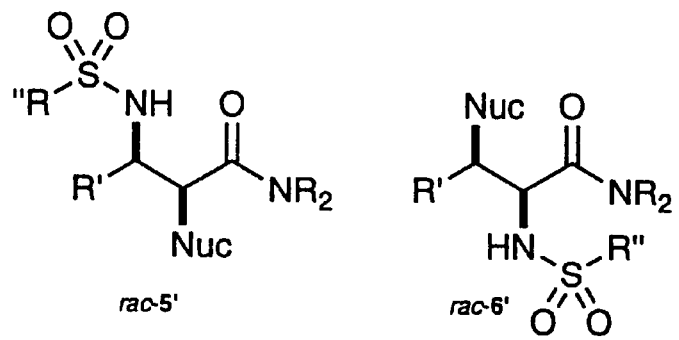
FIG. 9 illustrates the generalized structure for the α,β-substituted amino amides.
Figure 10A:
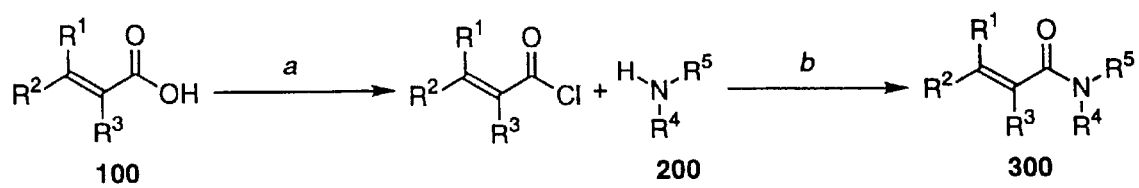
FIG. 10 illustrates the following (All 'R' groups defined below): A) the general synthesis of an acyclic α,β unsaturated amide; B) the general synthesis of an exocyclic α,β unsaturated amide wherein $1 \leq n \leq 5$; C) the general synthesis of an exocyclic α,β unsaturated amide wherein $0 \leq n \leq 4$; D) the general synthesis of an endocyclic α,β unsaturated amide wherein $0 \leq n \leq 4$; E) the general synthesis of a sulfonamide; F) the general synthesis of a N-chloro N-sodio sulfonamide; G) the general synthesis of a carbamate; H) the general synthesis of an N-chloro N-sodio carbamate.
Figure 10B:
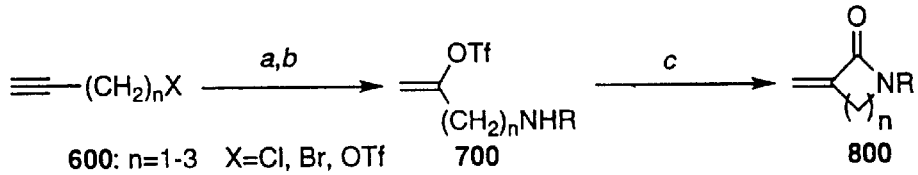
Figure 10C:
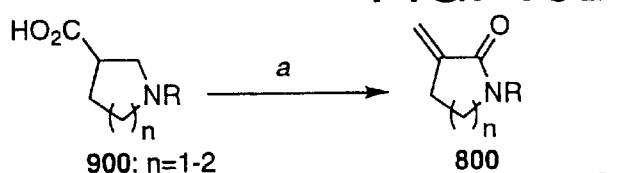
Figure 10D:
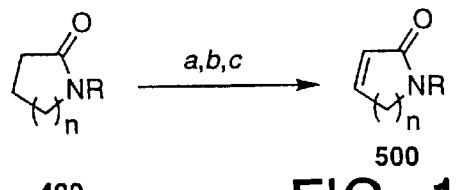
Figure 10E:
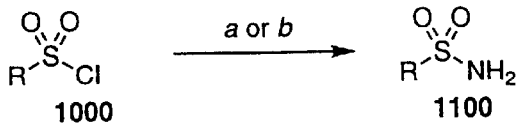
Figure 10F:
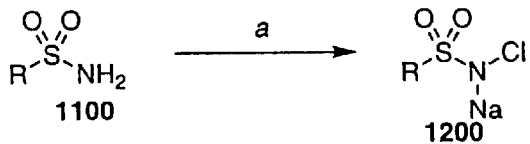
Figure 10G:
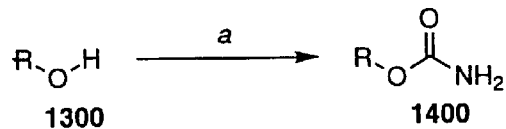
Figure 10H:
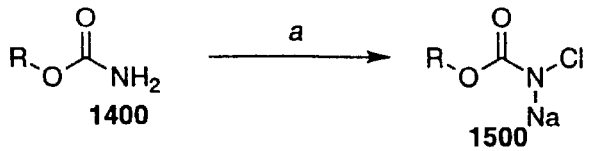
Figure 11:
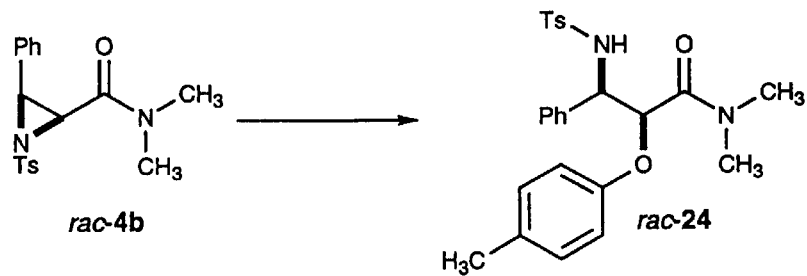
FIG. 11 shows the regiospecific, nucleophilic ring opening of the indicated aziridines with respective alcohol, thiol, and amine nucleophiles (first 4 schemes); the bottom scheme shows the hydrolysis of an α,β-substituted amide to a α,β-free acid using standard conditions suggested in the synthetic protocals.
Figure 11:
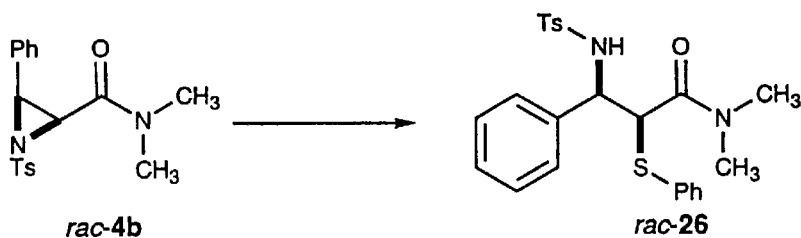
Figure 11:
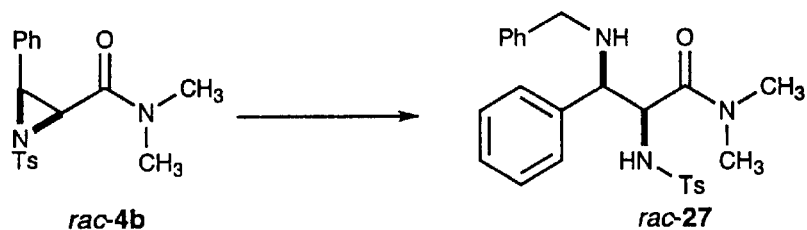
Figure 11:
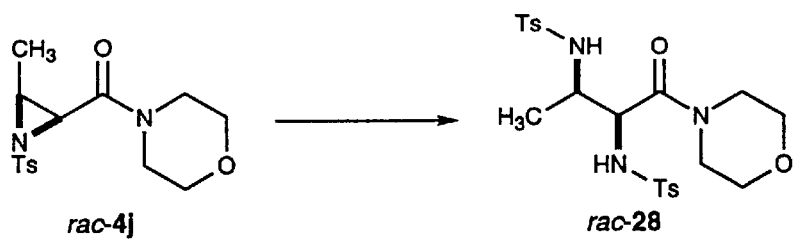
Figure 11:
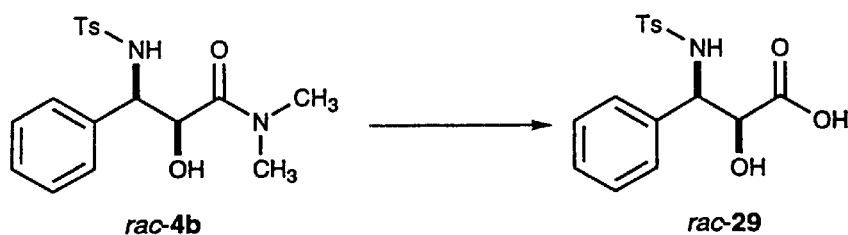
Figure 12A:
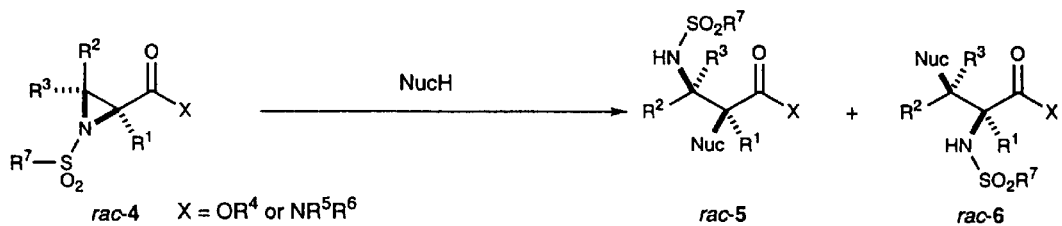
FIG. 12 shows the following: A) general scheme depicting products formed from ring opening of an aziridine with a nucleophile—note that one isomer is usually regioselectively favored over the other; B) AA process on acyclic α,β unsaturated amide; C) AA process on exocyclic α,β unsaturated amide; D) AA process on endocyclic α,β unsaturated amide; note that the R groups are as defined in the examples below and synthetic protocals.
Figure 12B:
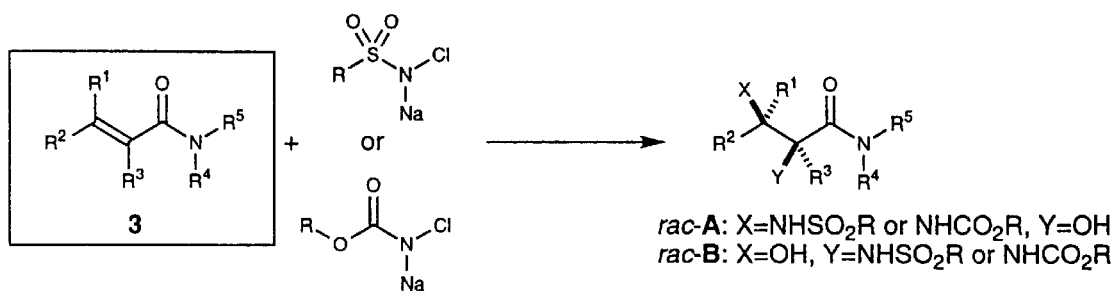
Figure 12C:
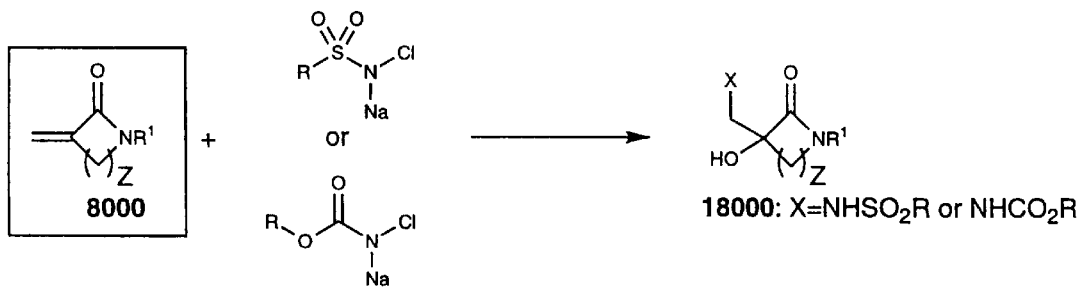
Figure 12D:
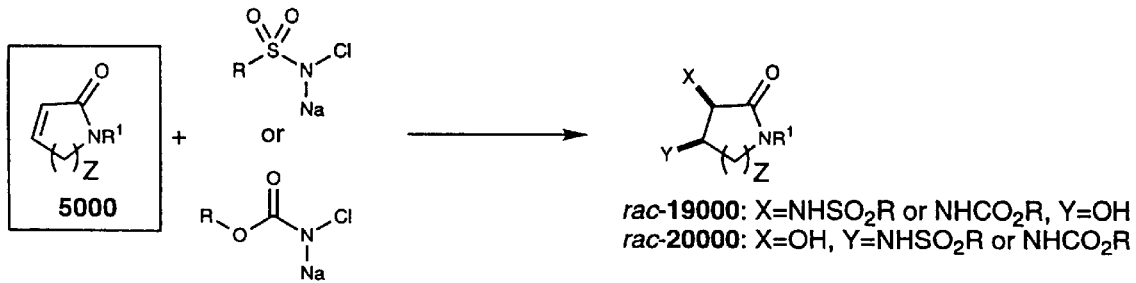
Figure 13A:
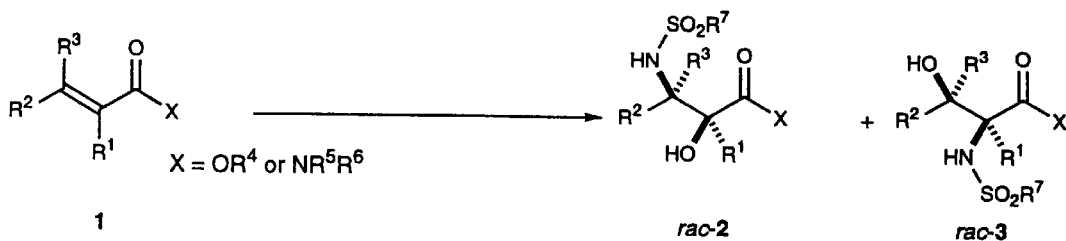
FIG. 13 illustrates A) AA process on acyclic α,β unsaturated amide; B) aziridine formation from the α,β-hydroxy amine products formed in step A using esters or amides; C) further shows aziridine formation from the α,β-hydroxy amine products formed in step A using amides—highlighting the formation of one, non racemic aziridine stereoisomer if ligands are used; D) general scheme depicting products formed from ring opening of an aziridine with a nucleophile—note that one isomer is usually regioselectively favored over the other; E) shows the hydrolysis of an α,β-substituted amide to α,β-free acid using standard conditions suggested in the synthetic protocals.
Figure 13B:
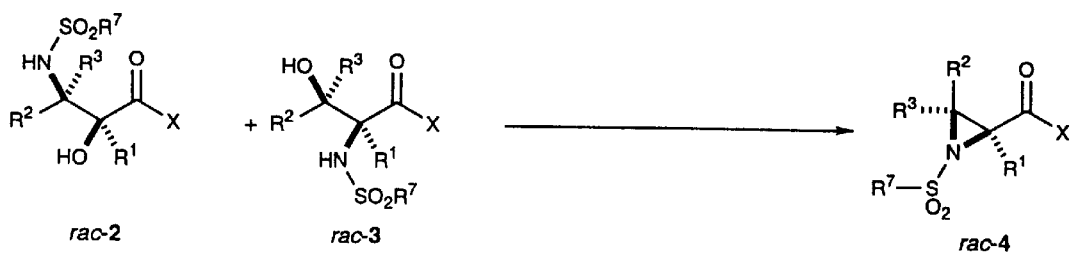
Figure 13C:
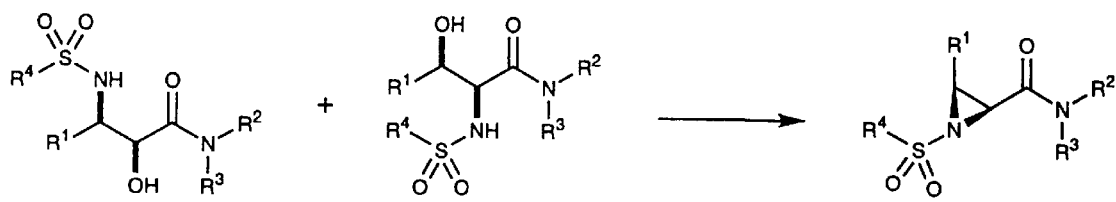
Figure 13D:
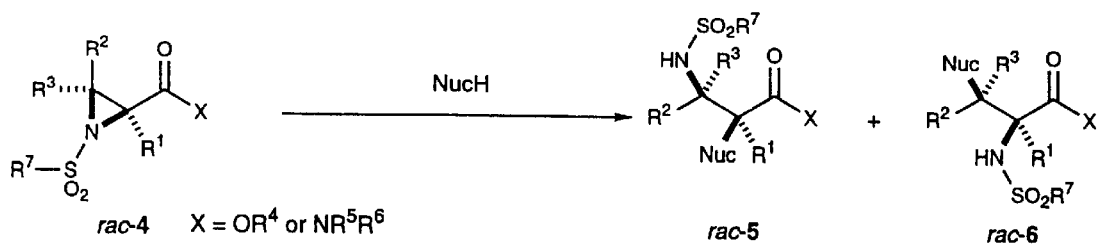
Figure 13E:
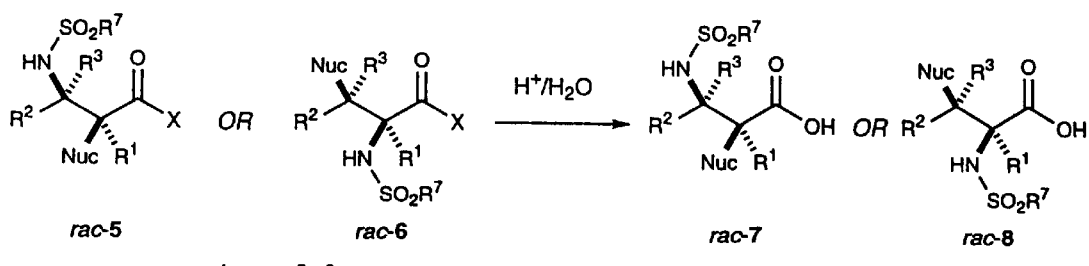

Thus, compounds having the general structures 5' and 6' (FIG. 9) are readily accessible in three steps from the unsaturated amides [the sulfonamide substituent (R") is indicated generically in FIG. 9 since alkyl sulfonamide analogs (e.g., R"=Me or n-Bu) also give excellent results in the aminohydroxylation step]. In addition, 5' and 6' offer four points of variability for the construction of combinatorial libraries and all of the chemical steps involved in their syntheses are easily automated. These steps are automatable due to the amazing efficiency of the unsaturated amide aminohydroxylation core reaction (FIG. 1).

Enormous libraries ($10^5$–$10^6$) of highly functionalized molecules can be easily available and rapidly constructed through this unique aminohydroxylation-based core chemistry. The range of nucleophiles which are successful in this sequence (FIG. 8) is only hinted at in this example and provides one of the more exciting areas where variability will result in the application of this process to the synthesis of biologically active molecules.

EXAMPLE 5

General Method for the Aminohydroxylation of α, β-unsaturated Amides or Esters (as Illustrated in FIG. 13 Scheme A)

The following is a standard procedure for the AA of olefins to form α,β-unsaturated amides or esters. To a stirred mixture of the α,β unsaturated amide or ester [1 equivalent], and a sulfonamide-based or carbamate-based chloramine salt [1–3 equivalents] in enough solvent to make the reaction mixture formally 0.1–3.0 M in the unsaturated amide is added $OSO_4$ $K_2OSO_2(OH)_4$ [0.04–1.0 mol %] in one portion at 0–60° C. The reaction mixture is stirred at that same temperature until tlc indicates that the starting α,β-unsaturated amide or ester has disappeared. Workup: Cases in which the products are insoluble in the reaction solution: Water [ca. 25–100% of the volume of the reaction solution] is added and the slurry is cooled in an ice/water bath until the temperature of the reation is ca. 5° C. The solid product is collected by filtration, washed twice with water [ca. 1–5 mL per gram of product per wash], and dried under a stream of air [or under vacuum] to afford the mixture of hydroxysulfonamide or hydroxycarbamate regioisomers.

Cases in which the products are soluble in the reaction solution: $Na_2SO_3$ [ca. 100–500 mg/mmol unsaturated amide] and ethyl acetate [ca. 1–20 mL/mmol unsaturated amide] are added and the slurry is stirred for 1–5 h. The phases are separated and the aqueous phase is washed with ethyl acetate until no product remains in the aqueous layer. The combined organic phases are shaken with brine, dried over $MgSO_4$ or $Na_4SO_4$ and evaporated to afford the mixture of hydroxysulfonamides or hydroxycarbamate regioisomers.

EXAMPLE 6

General Method for the Preparation of N-sulfonyl or N-cabamoyl Aziridine-2-Carboxamides or Aziridine-2-Carboxylic Esters (as Illustrated in FIG. 13 Scheme B)

To a stirred mixture of the of protected aminoalcohols [2 and 3, 1 equivalent) and a base [0–10 equivalents] in enough solvent[1] to make the reaction mixture formally 0.05–3.0 M in 2 and 3, is added, over 15–120 min, a suitable activating agent[2] for the hydroxyl moiety [1–3 equivalents] at a temperature in the range –80 to 30° C. After the addition is complete, the reaction is stirred for a further 30–120 min. A base [0–10 equivalents] is then added to initiate or complete the ring closure and the reaction is warmed to 0 to 100° C. The raction is stirred at this tempreature until the aziridine formation is complete (as determined by a suitable analytical method). Workup: The reaction is cooled or warmed to room temperature (if necessary) and evaporated to give the crude aziridine 4which is purified by an appropriate method. Alternatively, the reaction mixture is extracted with an aqueous acid (e.g., 1–2 M HCl) solution followed by an aqueous base (e.g., 1–2 M potassium carbonate or NaOH) solution. The organic phase is dried over $MgSO_4$ or $Na_2SO_4$ and evaporated to afford the crude aziridine 4 which is purified by an appropriate method.

EXAMPLE 7

General Method for the Preparation of Racemic Aziridines from Regioisomeric Mixtures of Hydroxysulfonamides Prepared from the Aminohydroxylation of α,β-Unsaturated Amides (as Illustrated in FIG. 13 Scheme C)

To a magnetically stirred solution of the mixture of hydroxysulfonamides (5.8 mol), obtained directly from the aminohydroxylation of α,β-unsaturated amides (vide supra), and $Et_3N$ (1.1 mL, 7.9 mmol) in $CH_2Cl_2$ (30 mL) under $N_2$ and cooled in an ice/$H_2O$ bath, is added methanesulfonyl chloride (0.58 mL, 7.5 mmol), dropwise, over 30 min. After the addition is complete, stirring is continued at 0° C. for a further 30 min before DBU (2.6 mL, 17.4 mmol) is added and the ice/water bath is removed. The reaction is stirred at RT until TLC indicates that the aziridine formation is complete (ca. 15 min to 1 h). The reaction mixture is extracted with 2N aqueous HCl (25 mL) followed by saturated aqueous $NaHCO_3$ (30 mL). The organic layer is dried over anhydrous $Na_4SO_4$, filtered, and concentrated under reduced pressure to give the N-sulfonylyl aziridine. Yield: 81%–99%.

EXAMPLE 8

General Method for the Regioselective Nucleophilic Opening of N-sulfonyl or N-cabamoyl Aziridine-2-carboxamides or Aziridine-2-carboxylic Esters (As Illustrated in FIG. 13 Scheme D)

Procedure: A stirred mixture of the of protected aziridine [4, 1 equivalent], a nucleophile [1–100 equivalents], and a catalyst [0.01–10 equivalents, if necessary], in enough solvent to make the reaction mixture formally 0.05–3.0 M in 4is stirred at a temperature in the range 20–160° C. The reaction is mainatined at that temperature until the aziridine has completely been converted to the ring-opened products.

Workup: The reaction is cooled or warmed to room temperature (if necessary) and evaporated to give the crude products 5 and 6 which are purified by an appropriate method. Alternatively, the reaction mixture is extracted with an aqueous acid (e.g., 1–2 M HCl) solution followed by an aqueous base (e.g., 1–2 M potassium carbonate or NaOH) solution. The organic phase is dried over $MgSO_4$ or $Na_4SO_4$ and evaporated to afford the crude aziridine 5 and 6 which are purified by an appropriate method.

EXAMPLE 9

General Method for the Hydrolysis of α,β-substituted Amino Amides and Esters to Give the α,β-substituted Amino Acids (as Illustrated in FIG. 13 Scheme E.)

A stirred solution of 5 or 6 [1 equivalent] in enough of a mixture of aqueous HCl [1–12 M] and a cosolvent (see below) to make the formal concentration of the substrate 0.05–3.0 M is heated at reflux until hydrolysis of the amide or ester moiety is complete. Workup: The reaction is cooled to room temperature and evaporated to give the crude acid 7 or 8 which is purified by an appropriate method. Alternatively, the reaction mixture is basified to pH~8–10 (e.g., using 1–2 M potassium carbonate or NaOH solution), and extracted with an organic solvent. The organic phase is washed with sat. Na bicarbonate and the combined aqueous phases are acidified to pH~1–2. The acid 7 or 8 precipetates and is obtained by filtration.

EXAMPLE 10

Scope of the Aminohydroxylation of Unsaturated Amides with a Variety of Aromatic Sulfonamides and Preparation of a Combinatorial Library Using Automated Methods The scope of the aminohydroxylation of unsaturated amides (Rubin et al. *Angew. Chem., Int. Ed. Engl.* 1997, 36, 2637–2640) with a variety of aromatic sulfonamides as nitrogen sources was investigated. This was accomplished by mixing unsaturated amides and chloramine salts of aromatic sulfonamides in a combinatorial fashion and adding $OSO_4$ to initiate the reactions. The liquid dispensing was automated using a Gilson 215 robotic liquid handler. Figure outlines the synthetic protocol which was used. The chloramines were generated by a standard procedure (scheme 1) Li et al. *Angew. Chem., Int. Ed. Engl.* 1996, 35, 2813–2817.

Figure 29:
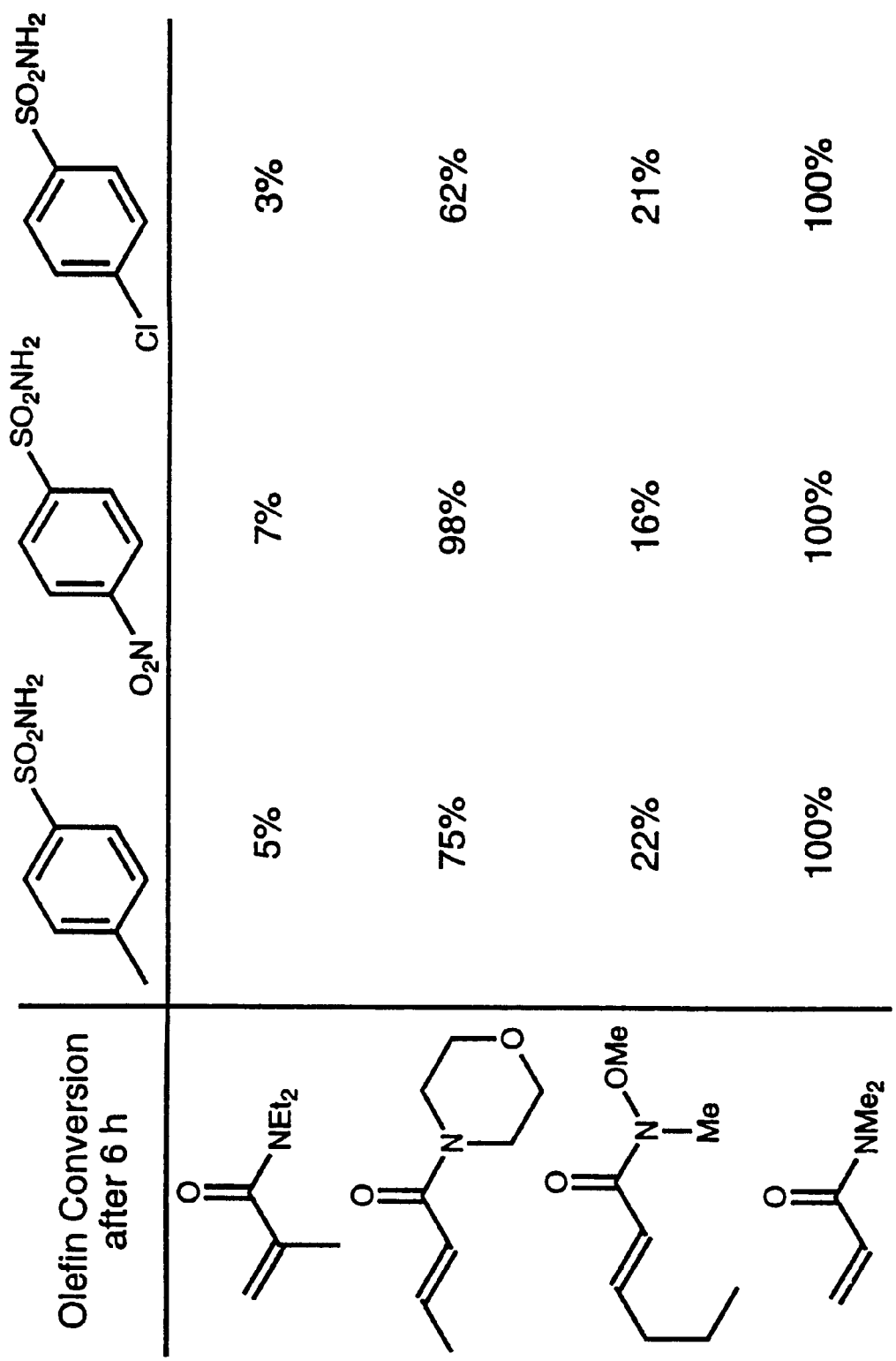
FIG. 29 shows the aminohydroxylation of alkyl-substituted unsaturated amides.
Figure 30:
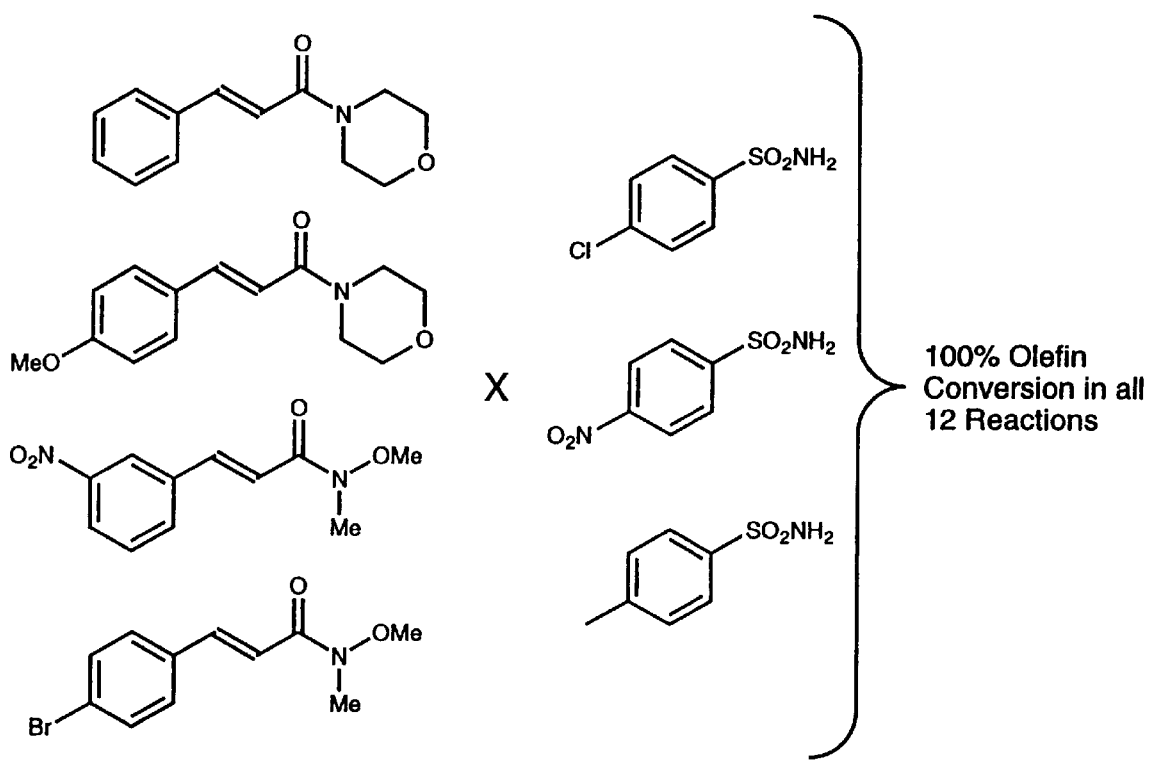
FIG. 30 illustrates the 100% conversion using the aminohydroxylation of selected cinnamides.

FIGS. 29 and 30 show the results from the aminohydroxylation of alkyl substituted amides and cinnamamides, respectively. In each case, the reactions were allowed to proceed for 6 h and then quenched with sodium sulfite and analyzed by HPLC against dimethylbenzamide as an internal standard. Each olefin/chloramine mixture showed clean conversion to the aminohydroxylation products, although after 6 hours reaction time, not all of the reactions had proceded to completion. However, in each cinnamamide case, clean and complete conversion to the aminohydroxylated products was observed in the 6 h reaction time period (FIG. 30).

Figure 31:
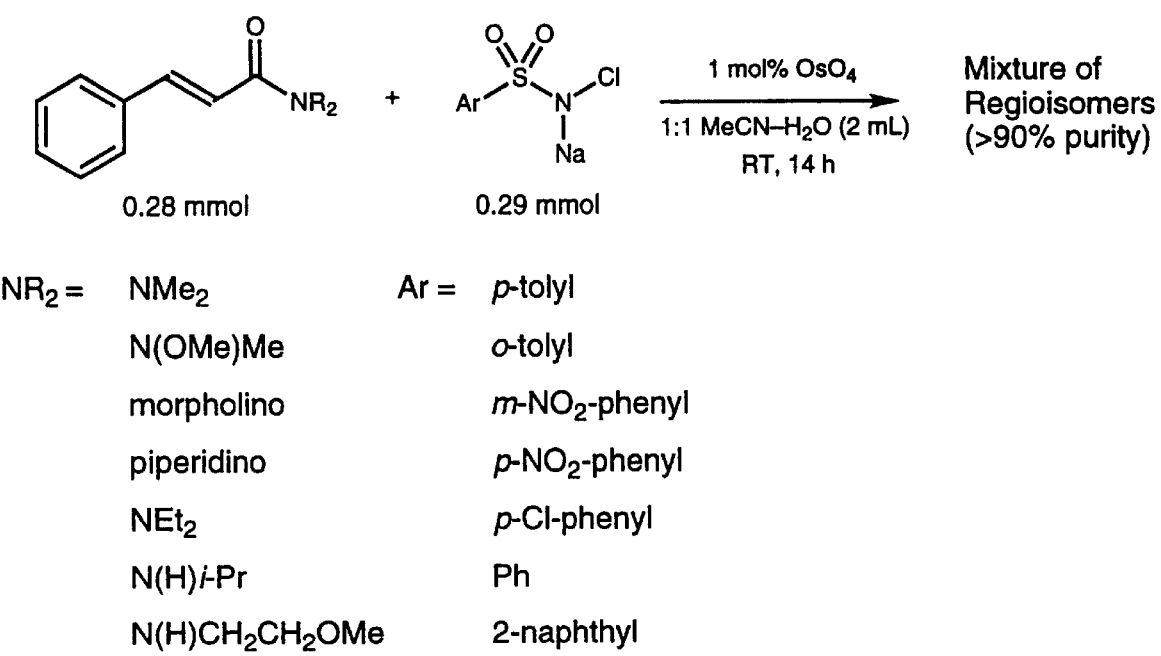
FIG. 31 illustrates the parrallel synthesis of a small-molecule library using the aminohydroxylation reaction.

Using these results, a 49 member library of hydroxysulfonamides was prepared. 7 aromatic sulfonamide chloramine salts (prepared as above) of varying electronic characteristics and 7 cinnamamides were mixed combinatorially in parralel reaction vessels (FIG. 31). $OSO_4$ was added to each reaction and the mixtures were stirred for 14 h. After reductive workup, HPLC indicated that the regioisomeric hydroxy sulfonamides were formed in >90% purity in each case (FIG. 31).

Figure 32:
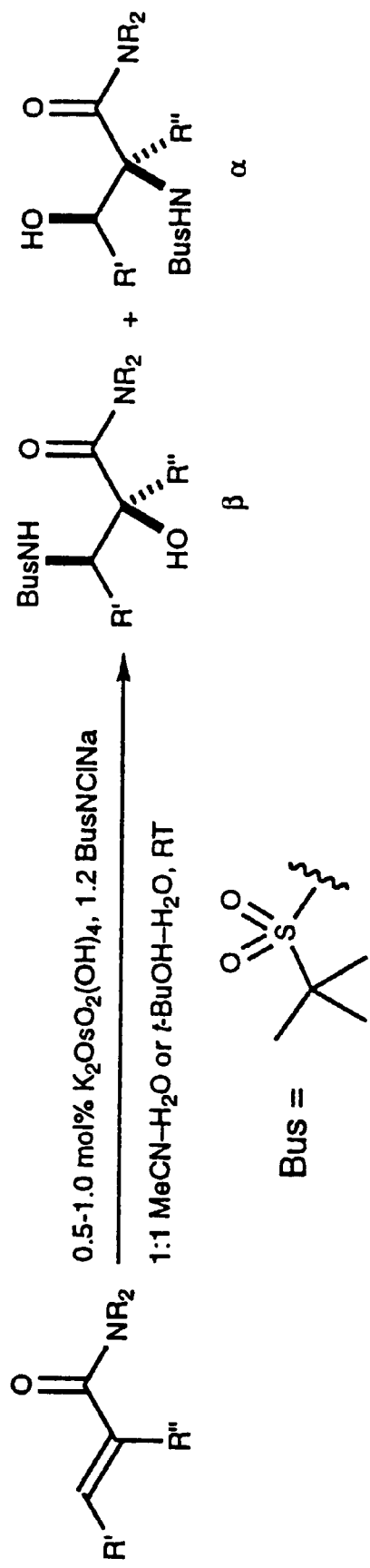
FIG. 32 shows the aminohydroxylation of unsaturated amides with BusNClNa.

EXAMPLE 11 t-Butylsulfonamide as a Nitogen Source for the Osmium-catalyzed Aminohydroxylation of Unsaturated Amides The reagent t-Butylsulfonamide ($BusNH_2$) was investigated as a nitrogen source for the osmium-catalyzed aminohydroxylation of unsaturated amides (Rubin et al. *Angew. Chem., Int. Ed. Engl.* 1997, 36, 2637–2640) The t-butylsulfonyl (Bus) protecting group for amines was introduced by Weinreb in 1997 (Sun et al. *J. Org. Chem.* 1997, 62, 8604–8608) and offers the advantage of ease of deprotection using typically, trifluoroacetic acid/anisole or triflic acid/anisole at room temperature. The $BusNH_2$ is prepared from t-butyldisulfide by the method outlined by Weinreb. This sulfonamide was converted to its N-sodio-N-chloro derivative by sequential reaction with NaOH and t-BuOCl according to a standard procedure (Li et al. *Angew. Chem., Int. Ed. Engl.* 1996, 35, 2813–2817) and used directly in the aminohydroxylation reaction as shown in FIG. 32.

FIG. 33 shows the yields and regioselectivities for a variety of unsaturated amides. The regioselectivity trend was the same as that observed for the aminohydroxylation with chloramine-T (i.e., the β isomer was the major product, see FIG. 31). In addition, the yields were very high, as with chloramine-T. In conclusion, $BusNH_2$ is an excellent nitrogen source for the aminohydroxylation of unsaturated amides.

EXAMPLE 12

Figure 34:
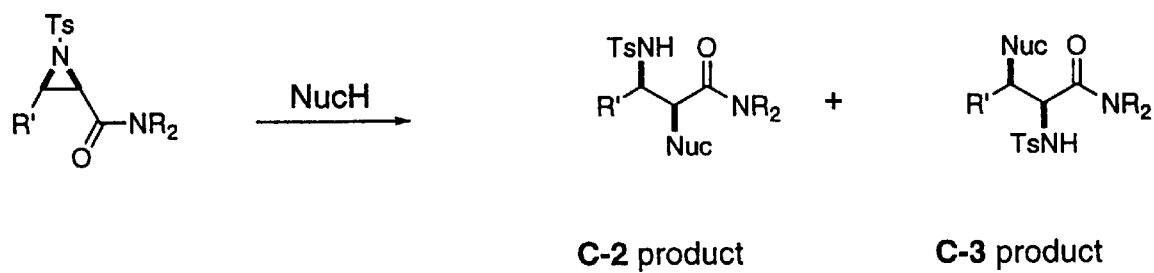
FIG. 34 shows the nucleophilic opening of aziridines.
Figure 35:
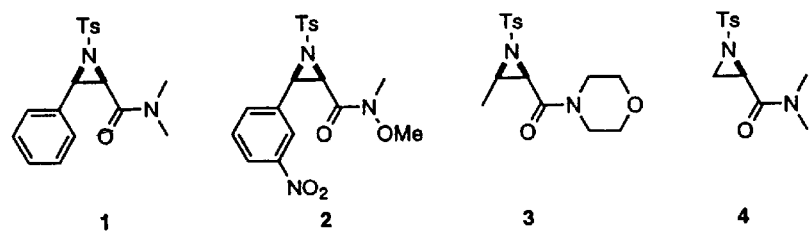
FIG. 35 highlights various aziridines investigated in exemplary nucleophilic opening reactions.

Further Discussion of Scope of the Nucleophilic Opening of Aziridines Derived from the Aminohydroxyulation of Unsaturated Amides The scope of the nucleophilic opening of aziridines derived from the aminohydroxyulation of unsaturated amides (Rubin et al. *Angew. Chem., Int. Ed. Engl.* 1997, 36, 2637 2640) was investigated (FIG. 34). Four aziridines (FIG. 35) were reacted with several amine, thiol, phenol, and sulfonamide nucleophiles and azide ion to determine the effect of the combinations on yield and regioselectivity (c-2:c-3, FIG. 34). In almost every case, the crude yield for the additions were quantitative. With thiol nucleophiles, the C-2 isomer was the only product observed with each of the aziridines. Phenol nucleophiles were C-2 selective with aziridines 4b and 4j, but the selectivities were lower for 4j than for 4b. Amine nucleophiles were highly c-3 selective for aziridine 4b, but the selectivities were lower for aziridine 4h and aziridines 4j and 4i exhibited almost no selectivity with some amines. A variety of sulfonamide nucleophiles were tested with aziridine 4b and were all found to be highly c-2 selective. In addition, the regioselectivity of the addition of azide to aziridine 4b could be switched from c-2 to c-3 selective by changing from basic to acidic conditions, respectively.

While a preferred form of the invention has been shown in the drawings and described, since variations in the preferred form will be apparent to those skilled in the art, the invention should not be construed as limited to the specific form shown and described, but instead is as set forth in the following claims.

Synthetic Protocals

General: All reactions were carried out under an argon atmosphere with dry, freshly distilled solvents under anhydrous conditions, unless otherwise noted. Tetrahydrofuran (THF), toluene and ethyl ether (ether) were distilled from sodium-benzophenone, and methylene chloride (Methylene chloride), from calcium hydride. Anhydrous solvents were also obtained by passing them through commercially available alumina column. Yields refer to chromatographically and spectroscopically ($^1H$ NMR) homogeneous materials, unless otherwise stated. Reagents were purchased at highest commercial quality and used without further purification unless otherwise stated. Reactions were monitored by thin layer chromatography carried out on 0.25 mm E. Merck silica gel plates (60F-254) using UV light as visualizing agent and 7% ethanolic phosphomolybdic acid or p-anisaldehyde solution and heat as developing agents. E. Merck silica gel (60, particle size 0.040–0.063 mm) was used for flash column chromatography. Preparative thin-layer chromatography (PTLC) separations were carried out on 0.25, 0.50 or 1 mm E. Merck silica gel plates (60F-254). NMR spectra were recorded on Brucker AMX-600 or AMX-500 instruments and calibrated using residual undeuterated solvent as an internal reference. The following abbreviations were used to explain the multiplicities: s=singlet, d=doublet, t=triplet, q=quartet, m=multiplet, b=broad. IR spectra were recorded on a Perkin-Elmer 1600 series FT-IR spectrometer. Optical rotations were recorded on a Perkin-Elmer 241 polarimeter. High resolution mass spectra (HRMS) were recorded on a VG ZAB-ZSE mass spectrometer under fast atom bombardment (FAB) conditions with NBA as the matrix. Melting points (mp) are uncorrected and were recorded on a Thomas Hoover Unimelt capillary melting point apparatus.

Aminohydroxylation procedure A (FIGS. 1–5)—when the products are insoluble in the reaction mixture—described for the aminohydroxylation of N,N-dimethylcinnamamide (1b): To a mechanically stirred solution of 1b (17.52 g, 100 mmol) and Chloramine-T trihydrate (35.2 g, 125 mmol) in a 1:1 (v:v) tBuOH-water mixture (130 mL), was added $K_2OsO_2(OH)_4$ (73.7 mg, 0.20 mmol, 0.20 mol %). As the catalyst dissolved (20–30 min), the supernatant became orange and then darkened to a deep orange-red once the solution was homogeneous. The reaction was stirred overnight at room temperature, during which time a fine precipitate had appeared. After this time, TLC (silica, $R_f$(1b)= 0.20, $R_f$(products)=0.15, 1:1 EtOAc-hexane, 2 developments) indicated that the olefin had been completely consumed. The endpoint of the reaction was accompanied by the color of the reaction solution fading back to yellow-orange. Water (50 mL) was added and the reaction slurry was cooled with stirring in an ice-water bath for 1 h. The solid product was collected by filtration and washed with water (2×50 mL). Drying under a stream of air overnight afforded the product (34.0 g, 94%) as a mixture of 2b and 3b in a 3.0:1 ratio, respectively. Recrystallization of a portion of this mixture from MeOH afforded analytically pure 2b as colorless blocks: m.p. 176–177° C. (sealed tube); $^1$H NMR (400 MHz, $CDCl_3$, TMS): δ=7.56–7.53 (m, 2H), 7.24–7.20 (m, 5H), 7.16–7.13 (m, 2H), 5.52 (d, J=6.1 Hz, 1H), 4.46 (dd, J=6.9, 4.4 Hz, 1H), 4.42 (dd, J=6.1, 4.4 Hz, 1H), 4.02 (d, J=6.9 Hz, 1H), 2.84 (s, 3H), 2.67 (s, 3H), 2.36 (s, 3H); anal. calcd for $C_{18}H_{22}N_2O_4S$: C, 59.65; H, 6.12; N, 7.73. Found: C, 59.68; H, 5.99; N, 7.76.

Aminohydroxylation procedure B (FIGS. 1–5)—when the products are soluble in the reaction mixture—described for the aminohydroxylation of N,N-dimethylacrylamide (1i): To a magnetically stirred solution of 1i (5.0 mL, 4.81 g, 48.5 mmol) and Chloramine-T trihydrate (14.0 g, 49.7 mmol) in a mixture of MeCN (50 mL) and water (50 mL), was added $K_2OsO_2(OH)_4$ (89.3 mg, 0.24 mmol, 0.50 mol %). The color changes described for procedure A were noted. After stirring overnight at room temperature, TLC (silica, $R_f$(1i)=0.27, $R_f$(products)=0.40, EtOAc) revealed that the olefin had been completely consumed. $Na_2SO_3$ (10 g) and ethyl acetate (50 mL) were added and the triphasic mixture was vigorously stirred for a further hour, during which time the solids completely dissolved. After separation of the phases and extraction of the aqueous phase with ethyl acetate (2×50 mL), the combined organic phases were shaken with brine (50 mL), dried over $Na_2SO_4$, filtered, and concentrated under reduced pressure to yield an oil. Trituration of the oil with diethylether (ca. 30 mL) followed by filtration afforded the solid product (13.8 g, 99%) as a mixture of 2i and 3i in a 10:1 ratio, respectively. Recrystallization of a portion of this mixture from MeOH afforded analytically pure 2i as colorless needles: m.p. 123–124° C. (sealed tube); $^1$H NMR (400 MHz, $CDCl_3$, TMS): δ=7.76–7.72 (m, 2H), 7.33–7.30 (m, 2H), 5.24–5.21 (m, 1H), 4.47–4.42 (m, 1H), 3.84 (d, J=7.4 Hz, 1H), 3.28 (ddd, J=13.2, 8.2, 3.2 Hz, 1H), 3.00 (s, 3H), 2.97 (s, 3H), 2.89 (ddd, J=13.2, 7.4, 4.4 Hz, 1H), 2.43 (s, 3H); anal. calcd for $C_{12}H_{18}N_2O_4S$: C, 50.34; H, 6.34; N, 9.78. Found: C, 50.34; H, 6.25; N, 9.79.

Preparation of aziridines 4 (FIGS. 4 and 5)—described for the preparation of rac-4b: To a magnetically stirred solution of the mixture of 2b and 3b (2.10 g, 5.8 mmol) and $Et_3N$ (1.1 mL, 7.9 mmol) in $CH_2Cl_2$ (30 mL) under $N_2$ and cooled in an ice-$H_2O$ bath, was added methanesulfonyl chloride (0.58 mL, 7.5 mmol), dropwise, over 30 min. After the addition was complete, stirring was continued at 0° C. for a further 30 min before DBU (2.6 mL, 17.4 mmol) was added and the ice-water bath was removed. After 15 min, TLC (silica, $R_f$(4b)=0.44, 4:1 EtOAc-hexane) indicated that the aziridine formation was complete. The reaction mixture was extracted with 2 N aqueous HCl (30 mL) followed by saturated aqueous $NaHCO_3$ (30 mL). The organic layer was dried over anhydrous $Na_2SO_4$, filtered, and concentrated under reduced pressure. Flash column chromatography on silica gel using EtOAc-hexane (3:1, v:v) as the eluent provided 4b (1.90 g, 95%) as a colorless solid: m.p. 130–131° C. (sealed tube); $^1$H NMR (400 MHz, $CDCl_3$, TMS): δ=7.98–7.95 (m, 2H), 7.35–7.33 (m, 2H), 7.30–7.26 (m, 5H), 4.14 (d, J=7.5 Hz, 1H), 3.79 (d, J=7.5 Hz, 1H), 2.90 (s, 3H), 2.70 (s, 3H), 2.42 (s, 3H); anal. calcd for $C_{18}H_{20}N_2O_3S$: C, 62.77; H, 5.85; N, 8.13. Found: C, 62.61; H, 5.69; N, 8.24.

Preparation of N,N-Dimethyl-(2R*,3S*)-2-hydroxy-3-phenyl-3-(p-toluenesulfonamido)-propanamide (rac-2b) and N,N-Dimethyl-(2R*,3S*)-3-hydroxy-3-phenyl-2-(p-toluenesulfonamido)-propanamide (rac-3b): To a mechanically stirred solution of N,N-dimethylcinnamamide (1b, 17.52 g, 100 mmol) and Chloramine-T trihydrate (35.2 g, 125 mmol) in a 1:1 (v:v) t-BuOH-water mixture (130 mL) was added $K_2OsO_2(OH)_4$ (73.7 mg, 0.20 mmol, 0.20 mol %). As the catalyst dissolved (20–30 min), the supernatant became orange and then darkened to a deep orange-red once the solution was homogeneous. The reaction was stirred overnight at room temperature, during which time a fine precipitate had appeared. After this time, TLC (silica, Rf(1b)=0.20, Rf(products)=0.15, 1:1 EtOAc-hexane, 2 developments) indicated that the olefin had been completely converted to the aminohydroxylated products. The endpoint of the reaction was accompanied by the color of the reaction solution fading back to yellow-orange. Water (50 mL) was added and the reaction slurry was cooled with stirring in an ice-water bath for 1 h. The solid product was collected by filtration and washed with water (2×50 mL). Drying under a stream of air overnight afforded the product (33.99 g, 94%) as a mixture of 2b and 3b in a 3.3:1 ratio, respectively. Recrystallization of a portion of this mixture from MeOH afforded analytically pure 2b as colorless blocks.

Preparation of 4-[(2R*,3S*)-2-Hydroxy-3-(p-toluenesulfonamido)butanoyl]-morpholine(rac-2e) and 4-[(2R*,3S*)-3-Hydroxy-2-(p-toluenesulfonamido) butanoyl]morpholine (rac-3e): To a magnetically stirred solution of 4-(2-butanoyl)morpholine (1e, 1.55 g, 10 mmol) and Chloramine-T trihydrate (2.87 g, 10 mmol) in a mixture of MeCN (10 mL) and water (10 mL) was added $K_2OsO_2(OH)_4$ (18.4 mg, 0.050 mmol, 0.50 mol %). After stirring overnight at room temperature, TLC (silica, EtOAc) revealed that the alkene had been completely consumed. $Na_2SO_3$ (5 g) and ethyl acetate (10 mL) were added. and the triphasic mixture was vigorously stirred for a further hour during which time the solids completely dissolved. After separation of the phases and extraction of the aqueous phase with ethyl acetate (2×10 mL), the combined organic phases were shaken with brine (10 mL), dried over $Na_2SO_4$, filtered, and concentrated under reduced pressure to yield an oil. Trituration of the oil with diethylether (ca. 20 mL) followed by filtration afforded the solid product (3.31 g, 97%) as a mixture of 2e and 3e in a 1:1.4 ratio, respectively.

Preparation of (2R*,3R*)-2-(N,N-dimethylcarbamoyl)-3-phenyl-1-(p-toluenesulfonyl)aziridine (rac-4b): To a magnetically stirred solution of a mixture of 2b and 3b (2b:=5:1, 2.10 g, 5.8 mmol) and $Et_3N$ (1.1 mL, 7.9 mmol) in CH2Cl2 (30 mL) under N2 and cooled in an ice-H2O bath, was added methanesulfonyl chloride (0.58 mL, 7.5 mmol), dropwise, over 30 min. After the addition was complete, stirring was continued at 0° C. for a further 30 min before DBU (2.6 mL, 17.4 mmol) was added and the ice-water bath was removed. After 15 min, TLC (silica, Rf(4b)=0.44, 4:1 EtOAc-hexane) indicated that the aziridine formation was complete. The reaction mixture was extracted with 2 N aqueous HCl (30 mL) followed by saturated aqueous NaHCO3 (30 mL). The organic layer was dried over anhydrous Na2SO4,filtered, and concentrated under reduced pressure. Flash column chromatography on silica gel using EtOAc-hexane (3:1, v:v) as the eluent provided 4b (1.90 g, 95%) as a colorless solid.

Preparation of (2R*,3R*)-3-methyl-2-(morpholine-N-carbonyl)-1-(p-toluenesulfonyl)aziridine (rac-4j): To a magnetically stirred solution of a mixture of 2j and 3j (2j:3j= 1:1.4, 1.50 g, 4.4 mmol) and Et3N (0.86 mL, 6.2 mmol) in CH2Cl2 (20 mL) under N2 and cooled in an ice-H2O bath, was added methanesulfonyl chloride (0.44 mL, 5.7 mmol), dropwise, over 30 min. After the addition was complete, stirring was continued at 0° C. for a further 30 min before DBU (2.0 mL, 13.4 mmol) was added and the ice-water bath was removed. After 30 min, TLC (silica, Rf(4j)=0.30, 4:1 EtOAc-hexane) indicated that the aziridine formation was complete. The reaction mixture was extracted with 2 N aqueous HCl (20 mL) followed by saturated aqueous NaHCO3 (20 mL). The organic layer was dried over anhydrous Na2SO4, filtered, and concentrated under reduced pressure. Flash column chromatography on silica gel using EtOAc-hexane (4:1, v:v) as the eluent provided 4j (1.30 g, 92%) as a colorless solid.

Nucleophilic Opening of Aziridines

Preparation of N,N-dimethyl-(2R*,3S*)-3-phenyl-2-thiophenoxy-3-(p-toluenesulfonamido)-propanamide (rac-26): A solution of 4b (100 mg, 0.29 mmol) and thiophenol (0.06 mL, 0.58 mmol) in DMF (0.5 mL) was heated to 60° C. (oil bath) under a nitrogen atmosphere. After 19 h, the reaction was cooled to room temperature, taken up in EtOAc (5 mL) and extracted with a 10% aqueous K2CO3 solution (2×5 mL). Enough CH2Cl2 (ca. 3 mL) was added to dissolve the solids and the new solution was washed with brine (5 mL), dried over MgSO4, filtered, and evaporated to yield 26 as a colorless solid in quantitative yield.

Preparation of N,N-dimethyl-(2R*,3S*)-3-benzylamino-3-phenyl-2-(p-toluenesulfonamido)-propanamide (rac-27): A mixture of 4b (100 mg, 0.29 mmol) and benzylamine (0.30 mL, 2.8 mmol) was heated to 100° C. (oil bath) under a nitrogen atmosphere. After 18 h, the reaction was cooled to room temperature, taken up in CH2Cl2 (1 mL) and chromatographed on silica [1:1–3:7 hexanes-EtOAc (0.1% NEt3)] to give 27 (127 mg, 97%) as a colorless solid.

Preparation of N,N-dimethyl-(2R*,3S*)-3-(p-methylphenoxy)-3-phenyl-2-(p-toluenesulfonamido)-propanamide (rac-24): $K_2CO_3$ (133 mg, 0.96 mmol) was suspensed in a magnetically stirred solution of 4b (100 mg, 0.29 mmol) and p-cresol (0.10 mL, 0.96 mmol) in DMF (0.5 mL) under N2. The mixture was heated to 100° C. (oil bath) for 24 h and then cooled to room temperature. The reaction mixture was partitioned between EtOAc (10 mL) and water (5 mL) and the phases were separated. The organic phase was washed with brine (2×5 mL), dried over anhydrous Na2SO4, filtered, and concentrated under reduced pressure. Flash column chromatography on silica gel using EtOAc-hexane (1:1–3:2, v:v) as the eluent provided 24 (121 mg, 92%) as a colorless solid.

Preparation of 4-[(2R*,3S*)-2,3-bis(p-toluenesulfonamido)-butanoyl]-morpholine (rac-28): A magnetically stirred suspension of K2CO3 (276 mg, 2.0 mmol), 4j (324 mg, 1.0 mmol), and p-toluenesulfonamide (171 mg, 1.0 mmol) in DMF (1.0 mL) was heated to 100° C. (oil bath) under N2. After 24 h, the reaction was cooled to room temperature, partitioned between EtOAc (10 mL) and 2 N HCl (10 mL), and the phases wre separated. The organic phase was washed with water (2×10 mL) followed by brine (10 mL), dried over anhydrous Na2SO4, filtered, and concentrated under reduced pressure to give 28 (479 mg, 97%) as a colorless solid.

Hydrolysis of an amide to an acid Preparation of (2R*,3S*)-2-hydroxy-3-phenyl-3-(p-toluenesulfonamido)-propanoic acid (rac-29): A solution of 4b (1.00 g, 2.76 mmol) in 20% aqueous HCl (10 mL) and 1,4-dioxane (10 mL) was heated to reflux under N2 for 7 h. After this time, the reaction was cooled to room temperature and basified to pH~8 by adding solid K2CO3. The aqueous solution was extracted with EtOAc (3×10 mL) and the combined organic layers were washed with saturated aqueous NaHCO3 (10 mL). The aqueous phases were combined, filtered and cooled in an ice-water bath. Once cool, the solution was acidified to pH~1 with conc. HCl. Filtration afforded 29 (860 mg, 93%) as a white powder.

Sources of Starting Materials: $\alpha,\beta$-Unsaturated amides with acyclic double bonds as illustrated in FIG. 10, SCHEME A: Reaction conditions: (a) oxalyl chloride, $CH_2Cl_2$, cat. DMF, RT to reflux; (b) $K_2CO_3$, $H_2O$, $CH_2Cl_2$, 0° C. Typical experimental procedure: A solution of the $\alpha,\beta$-unsaturated carboxylic acid (100, 100 mmol), oxalyl chloride (100 mmol), and DMF (200 mL) in $CH_2Cl_2$ (250 mL) is stirred at room temperature for 30 min and then heated to reflux (oil bath at 50° C.) for a further 30 min. The reaction is then cooled in an ice/water bath for 30 min and added (via cannula or dropping funnel), over 30 min, to a pre-cooled (ice/water bath) solution of the amine (200, 100 mmol) or its hydrochloride salt and $K_2CO_3$ (250 mmol). After stirring at 0° C. for a further 2 h, the phases are separarted and the organic layer is washed with 2N HCl (200 mL) followed by saturated aqueous NaHCO3 (200 mL), dried over MgSO4, and filtered. The volatiles are removed in vacuo to afford the crude $\alpha,\beta$-unsaturated amide (300) which is prurified by distillation under reduced pressure or by recrystallization. Yield: 85%–99%.

Sources of Starting Materials as illustrated in FIG. 10, SCHEME B: $\alpha,\beta$-Unsaturated amides with exocyclic double bonds: Reaction conditions: (a) TfOH, $CHCl_3$, RT; (b) $BnNH_2$, $CHCl_3$, reflux; (c) 10 mol % Pd(PPh3)4, Bu3N, CO (1 atm), CH3CN, 65° C. Typical experimental procedure for the preparation of 700—described for the case in which n=1, X=Br, and R=Bn: Triflic acid (2.32 mL, 26.23 mmol) was added dropwise under $N_2$ over 10 min to a stirred solution of propargyl bromide (2.0 mL, 26.23 mmol) in CHCl3 (30 mL) at 0° C. The ice bath was removed and the dark solution was stirred at RT for 60 min, followed by the addition of pyridine (5 mL). The solution was washed with water (50 mL) and dil. hydrochloric acid (2×50 mL). The organic phase was dried and the solvent evaporated. The residue was purified by Kugelrohr distillation to yield 1-bromo-2-[(trifluoromethanesulfonyl]oxy]prop-2-ene as a colorless liquid. A solution of benzylamine (81 mL, 0.74 mmol) in $CHCl_3$ (4 mL) was added dropwise to a mixture of 1-bromo-2-[(trifluoromethanesulfonyl)oxy]prop-2-ene (0.37 mmol) and Et3N (0.1 mL, 0.74 mmol) in $CHCl_3$ (4 mL) at 1° C. The solution was then heated at reflux for 15 h. The mixture was washed with water (10 mL), the organic extracts were dried and the solvent was evaporated. The residue was purified by flash chromatography (hexanes-EtOAc, 9:1) to yield N-benzyl-2-[(trifluoromethanesulfonyl)oxy]-2-propenylamine as a pale yellow solid. Yield: 55%. Next, for the case in which n=1 and R=Bn: Carbon monoxide was bubbled through a solution of N-benzyl-2-[(trifluoromethanesulfonyl)oxy]-2-propenylamine (0.36 mmol), Pd(PPh3)4 (0.041 g, 0.036 mmol), tri-n-butylamine (0.17 mL, 0.72 mmol) in acetonitrile (15 mL) for 25 min. The reaction was then heated to 65° C. for 5 h. The solution was then allowed to cool to room temperature upon which ether (15 mL) was added and the solution filtered through a pad of kenite. The pad was subsequently thoroughly rinsed with ether (3×10 mL). The solvent was then removed in vaccuo and the residue taken up in dichloromethane. Flash chromatography (hexanes:ethyl acetate; 19:1) twice yielded 1-benzyl-3-methyleneazetidinone as a white amorphous solid. Yield: 73%.

General experimental procedure for the preparation of 800 FIG. 10, Scheme C: Reaction conditions: (a) Ac2O, reflux Typical experimental procedure for the preparation of 8: To 10 mmol of the cyclic β-aminoacid (900) was added 100 mL of acetic anhydride. The solution was then heated at reflux for 3 h under nitrogen, cooled, poured into an aqueous solution of potassium carbonate (100 g in 200 mL of H2O), and stirred for 4h at 0° C. At the end of this time additional potassium carbonate was added, if necessary, to adjust the pH to 8. The aqueous solution was then extracted with chloroform (3×100 mL), and the chloroform extracts were combined, dried over magnesium sulfate, filtered, and evaporated to yield the lactam (8). Yield: 40%–95%. α,β-Unsaturated amides with endocyclic double bonds: preparation General experimental procedure for the preparation of 300 FIG. 10, Scheme D: Reaction conditions: (a) 1. NaH, THF, 0° C. to RT; 2. RCl; (b) 1. LDA, THF, –78° C.; 2. PhSeCl, HMPA, THF, –78° C. to RT; (c) MCPBA, $CH_2Cl_2$, 0° C. to RT. Typical experimental procedure for the preparation of 5-described for the case in which n=2 and R=Bn: Sodium hydride dispersion in oil (60%, 2.08 g, 52.0 mmol) was washed with anhydrous hexane (3×10 mL) under argon atmosphere, resuspended in dry THF (50 mL), and cooled to 0° C. A solution of d-valerolactam (97%, 4.65 g, 45.5 mmol) in dry THF (200 mL) was slowly added to the former suspension. The mixture was stirred at 0° C. for 30 min, and at room tempreature until cessation of hydrogen evolution. Benzyl chloride (5.2 mL, 45.4 mmol) was added dropwise under argon atmosphere, and the new mixture was refluxed until completion of the alkylation was observed on tlc (48 h). The reaction was quenched with H2O (200 mL), the layers were separated, and the aqueous phase was extracted first with Et2O then with $CH_2Cl_2$. The combined organic extracts were dried, and the solvent and the remaining. benzyl chloride were evaporated under vaccum to furnish N-benzyl-2-piperidone as a pale oil, which was used without purification. Yield: 69%. To a solution of N-benzyl-2-piperidone (2.0 g, 10.6 mmol) in dry THF (20 mL), cooled at –78° C. and under argon atmosphere, a solution of LDA (1.5 M, 14.84 mL, 22.3 mmol) was added dropwise. After stirring for 10 min, a solution of phenylselenyl chloride (97%, 2.09 g, 10.6 mmol) and HMPA (97%, 2.87 g, 15.9 mmol) in dry THF (20 mL) was slowly added at –78° C. The resulting orange solution was maintained at –78° C. for 20 min and left to reach room temperature. The reaction mixture was poured on H2O and extracted with Et2O. The combined organic extracts were subsequently washed with 10% aqueous NaOH, H2O, 10% aqueous HCl, and brine. The organic phase, dried and evaporated yielded an oil which was flash chromatographed (Et2O) to obtain N-benzyl-3-phenylselenyl-2-piperidone as a transparent brown oil. Yield: 69%. To a solution of N-benzyl-3-phenylselenyl-2-piperidone (2.69 g, 7.82 mmol) in $CH_2Cl_2$ (35 mL), cooled at 0° C., a solution of MCPBA (50%, 3.37 g, 9.76 mmol) in $CH_2Cl_2$ (40 mL) was slowly added. The mixture was allowed to reach room temperature and was stirred overnight (16 h). The crude reaction mixture was poured on a saturated aqueous NaHCO3 solution, dried and evaporated to yield an oil which was flash chromatographed (9:1 Et2O:MeOH) to yield pure N-benzyl-D3-piperidein-2-one. Yield: 90%.

General experimental procedure for the preparation of 1100 FIG. 10, Scheme E: Sulfonamides: preparation. Some sulfonamides are commercially available. Others are prepared from commercially available. sulfonyl chlorides: Reaction conditions: (a) NH3 (g), $CH_2Cl_2$, RT; (b) aqueous NH3, acetone, RT. Typical experimental procedure using gaseous ammonia: The sulfonyl chloride (1000, 10 mmol) is added slowly, in portions, to a stirred saturated solution of NH3 in $CH_2Cl_2$ (10 mL) at room temperature (NH3 (g) bubbled through the solvent beforehand). After the complete addition of 10, NH3 (g) is bubbled through the the reaction for a further 30 min. The solvent is then removed under reduced pressure to afford the crude sulfonamide (1100) which is purified by recrystallyzation from either acetone/water or from ethyl acetate/hexane. Yield: 80–95%. Typical experimental procedure using aqueous ammonia: To a stirred 30% aqueous ammonia solution (40 mL), is added the sulfonyl chloride (1000, 60 mmol) slowly, in portions. After the complete addition of 10, the reaction is stirred at room temperature overnight. The reaction is then filtered to collect the crude sulfonamide (1100) which is purified by recrystallyzation from either acetone/water or from ethyl acetate/hexane. Yield: 80–90%.

General experimental procedure for the preparation of 1200 FIG. 10, Scheme F: Chloramine salts of sulfonamides: preparation. Some chloramine salts of sulfonamides are commercially available (e.g Chloramine-T, Chloramine-B). Others are prepared from commercially available sulfonamides or sulfonamides prepared from commercially available sulfonyl chlorides (vide supra). Reaction conditions: (a) NaOH, t-BuOCl, H2O, RT. Typical experimental procedure for the preparation of 12—described for the case in which 1100 is methanesulfonamide. To a stirred solution of methanesulfonamide (4.81 g, 50 mmol) and sodium hydroxide (2.0 g, 50 mmol) in 40 mL of water was added slowly tert-butylhypochlorite (5.63 mL, 5.4 g, 50 mmol). The solution was stirred for 1 h and concentrated to dryness in vaccuo. After one trituration with with diethylether the pure salt sodium N-chloromethanesulfonamide was obtained. Yield: quantitative. The in situ generation of the chloramine salt is accomplished in the same way except the chloramine salt is used as the aqueous solution prior to evaporation in the above procedure.

General experimental procedure for the preparation of 1400 FIG. 10, Scheme G: Carbamates: preparation. Some carbamates are commercially available. Others are prepared from commercially available alcohols: Reaction conditions: (a) NaOCN, CF3COOH. Typical experimental procedure for the preparation of 1400-described for the case in which 1300 is t-butanol: A solution of 14.8 g (0.20 mole) of t-butyl alcohol in 125 mL of benzene is placed in a 500 mL three-necked flask equipped with a stirrer, a thermometer, and an addition funnel, and 26.0 g (0.40 mole) of sodium cyanate is added. The suspension is stirred as slowly as possible (ca. 120 rpm) while 48.0 g (31.2 mL, 0.42 mole) of trifluoroacetic acid is added dropwise at a rapid rate. The temperature slowly rises to about 37° after three-quarters of the trifluoroacetic acid has been added (ca. 7 minutes). At this point the mixture is cooled to 33–35° by brief immersion in an ice-water bath, then the addition is continued. When the addition of the acid is completed (10–12 minutes total time), the temperature slowly rises to 40° and then gradually subsides. Slow stirring is continued overnight at room temperature. The mixture is treated with 35 mL of water and stirred vigorously for a few minutes. The benzene layer is decanted, and the aqueous slurry is rinsed with two 125 mL portions of benzene. The combined organic extracts are washed once with 100 mL of aqueous 5% sodium hydroxide and with 100 mL of water, dried over anhydrous magnesium sulfate, and filtered. The solvent is removed by distillation under reduced pressure from a water bath kept at 30° to give t-butyl carbamate as white needles. Yield: 76–94%.

General experimental procedure for the preparation of 1500 FIG. 10, Scheme H: Chloramine salts of carbamates: preparation The chloramine salts of carbamates, although they can be isolated and stored for short periods, are usually pepared as aqueous solutions and used immediately. Reaction conditions: (a) NaOH, t-BuOCl, H2O, RT. Typical experimental procedure for the preparation of 15—described for the case in which 1400 is benzyl carbamate: Benzyl carbamate (0.469 g, 3.10 mmol) was dissolved in 4 mL n-propyl alcohol in a 20-mL scintillation vial equiped for magnetic stirring. To this stirred solution was added a freshly prepared solution of NaOH (0.122 g, 3.05 mmol in 7.5 mL of water), followed by freshly prepared tert-butyl hypochlorite 0.331 g, 3.05 mmol, ca. 0.35 mL).

Suitable nucleophiles for the ring-opening of N-sulfonyl or N-cabamoyl aziridine-2-carboxamides or aziridine-2-carboxylic esters as shown in FIG. 12—FIG. 12 illustrates the ring opening of aziridines with nucleophiles "NuH" which are selected from the following groups:

1) alcohols (ROH), thiols (RSH) and selenols (RSeH) wherein R is selected from the following: (a) C-atom-containing neighboring groups: H, methyl, ethyl, propyl, isopropyl, cyclopropyl, butyl, isobutyl, sec-butyl, tert-butyl, cyclobutyl, methylcyclopropyl, pentyl and isomers, hexyl and isomers, heptyl and isomers, octyl and isomers, nonyl and isomers, decyl and isomers, etc., alkynyl functionalities, benzyl with all kinds of substituted phenyl rings, alkyl groups containing the following functionalities: F, Cl, Br, CN, OH, C(O) (ketones), R—O—R (ethers), COOH (acids), C(O)OR (esters, lactones), C(O)NRR' (amides, lactames), SO3H (sulfonic acids), SO2OR (sulfonic acid esters), SO2NRR' (sulfonamides), R—SO2—R' (sulfones), NO2 (nitro-cpds.), phosphonic acid derivs., phosphorous acid derivs., phenyl, monosubstituted phenyl (2, 3, or 4), disubstituted phenyl (2,3 or 2,4 or 2,5 or 2,6 or 3,4 or 3,5), trisubstituted phenyl (2,3,4 or 2,3,5 or 2,3,6 or 3,4,5 or 3,4,6) or tetrasubstituted phenyl (2,3,4,5 or 2,3,5,6 or 2,4,5,6) or persubstituted phenyl or naphthyl, indenyl and any other kind of aromatic system with any substitution pattern, heteroaromatic systems with all kind of heteroatoms and substituents, directly attached carbonyl functionalities: R=COOH (acids), CO2R (esters), CONRR' (amides), C(O) (ketones) with R=H or different alkyl, substituted alkyl, aromatic groups and mixed versions, directly attached sulfonyl functionalities: R=SO3H (sulfonic acids), SO3R (sulfonic acid esters), SO2NRR' (sulfonamides), SO2R (sulfones) with R=H or different alkyl, substituted alkyl, aromatic groups and mixed versions; (b) heteroatoms: R=CN, F, Cl, R=OR, NRR' with R=H or different alkyl, substituted alkyl, aromatic groups and mixed versions 2) amines R—NH—R' wherein R=R'=X or R=X, R'=Y. where X and Y are selected from the group consisting of: (a) C-atom-containing neighboring groups: H, methyl, ethyl, propyl, isopropyl, cyclopropyl, butyl, isobutyl, sec-butyl, tert-butyl, cyclobutyl, methylcyclopropyl, pentyl and isomers, hexyl and isomers, heptyl and isomers, octyl and isomers, nonyl and isomers, decyl and isomers, etc., alkynyl functionalities, benzyl with all kinds of substituted phenyl rings, alkyl groups containing the following functionalities: F, Cl, Br, CN, OH, C(O) (ketones), R—O—R (ethers), COOH (acids), C(O)OR (esters, lactones), C(O)NRR' (amides, lactames), SO3H (sulfonic acids), SO2OR (sulfonic acid esters), SO2NRR' (sulfonamides), R—SO2—R' (sulfones), NO2 (nitro-cpds.), phosphonic acid derivs., phosphorous acid derivs., phenyl, monosubstituted phenyl (2,3, or 4), disubstituted phenyl (2,3 or 2,4 or 2,5 or 2,6 or 3,4 or 3,5), trisubstituted phenyl (2,3,4 or 2,3,5 or 2,3,6 or 3,4,5 or 3,4,6) or tetrasubstituted phenyl (2,3,4,5 or 2,3,5,6 or 2,4,5,6) or persubstituted phenyl or naphthyl, indenyl and any other kind of aromatic system with any substitution pattern, heteroaromatic systems with all kind of heteroatoms and substituents, directly attached carbonyl functionalities: X,Y=COOH (acids), CO2R (esters), CONRR' (amides), C(O) (ketones) with X,Y=H or different alkyl, substituted alkyl, aromatic groups and mixed versions, directly attached sulfonyl functionalities: X,Y=SO3H (sulfonic acids), SO3R (sulfonic acid esters), SO2NRR' (sulfonamides), SO2R (sulfones) with X,Y=H or different alkyl, substituted alkyl, aromatic groups and mixed versions;

3) heteroatoms: X,Y=CN, F, Cl; X,Y=OR, NRR' with X,Y=H or different alkyl, substituted alkyl, aromatic groups and mixed versions 4) amides RCONHR, RNHCONR'R'', RNHCOOR', RSONHR, RR'PONHR'', RSO2NHR'
   (i) R,R',R''=H
   (ii) R=X, R', R''=H
   (iii) R=X, R'=Y, R''=H
   (iv) R=X, R'=Y, R'=H
   (v) R=X, R',R''=H
   (vi) R=X, R'=Y, R''=Z
   wherein X, Y, and Z are selected from the group consisting of: (a) C-atom-containing neighboring groups: H, methyl, ethyl, propyl, isopropyl, cyclopropyl, butyl, isobutyl, sec-butyl, tert-butyl, cyclobutyl, methylcyclopropyl, pentyl and isomers, hexyl and isomers, heptyl and isomers, octyl and isomers, nonyl and isomers, decyl and isomers, etc., alkynyl functionalities, benzyl with all kinds of substituted phenyl rings, alkyl groups containing the following functionalities: F, Cl, Br, CN, OH, C(O) (ketones), R—O—R (ethers), COOH (acids), C(O)OR (esters, lactones), C(O) NRR' (amides, lactames), SO3H (sulfonic acids), SO2OR (sulfonic acid esters), SO2NRR' (sulfonamides), RSO2—R' (sulfones), NO2 (nitro-cpds.), phosphonic acid derivs., phosphorous acid derivs., phenyl, monosubstituted phenyl (2, 3, or 4), disubstituted phenyl (2,3 or 2,4 or 2,5 or 2,6 or 3,4 or 3,5), trisubstituted phenyl (2,3,4 or 2,3,5 or 2,3,6 or 3,4,5 or 3,4,6) or tetrasubstituted phenyl (2,3,4,5 or 2,3,5,6 or 2,4,5,6) or persubstituted phenyl or naphthyl, indenyl and any other kind of aromatic system with any substitution pattern, heteroaromatic systems with all kind of heteroatoms and substituents, directly attached carbonyl functionalities: X,Y,Z=COOH (acids), CO2R (esters), CONRR' (amides), C(O) (ketones) with X,Y,Z=H or different alkyl, substituted alkyl, aromatic groups and mixed versions, directly attached sulfonyl functionalities: X,Y,Z=SO3H (sulfonic acids), SO3R (sulfonic acid esters), SO2NRR' (sulfonamides), SO2R (sulfones) with X,Y,Z=H or different alkyl, substituted alkyl, aromatic groups and mixed versions;(b) heteroatoms:X,Y,Z=CN, F, Cl; X,Y,Z=OR, NRR' with X,Y,Z=H or different alkyl, substituted alkyl, aromatic groups and mixed versions 5. halogens, pseudohalogens salts of CN—, N3—, OCN—, SCN—, Cl—, I—, F—, Br—, etc
6. Organometallics such as Grignards (RMgX), alkyl lithiums (RLi), and cuprates (R2CuLi), higher order cuprates, organozincs (R2Zn), etc: where R is selected from the group consisting of:(a) C-atom-containing neighboring groups: H, methyl, ethyl, propyl, isopropyl, cyclopropyl, butyl, isobutyl, sec-butyl, tert-butyl, cyclobutyl, methylcyclopropyl, pentyl and isomers, hexyl and isomers, heptyl and isomers, octyl and isomers, nonyl and isomers, decyl and isomers, etc., alkynyl functionalities, benzyl with all kinds of substituted phenyl rings, alkyl groups containing the following functionalities: F, Cl, Br, CN, OH, C(O) (ketones), R—OR (ethers), COOH (acids), C(O)OR (esters, lactones), C(O)NRR' (amides, lactames), SO3H (sulfonic acids), SO2OR (sulfonic acid esters), SO2NRR' (sulfonamides), RSO2—R' (sulfones), NO2 (nitro-cpds.), phosphonic acid derivs., phosphorous acid derivs., phenyl, monosubstituted phenyl (2, 3, or 4), disubstituted phenyl (2,3 or 2,4 or 2,5 or 2,6 or 3,4 or 3,5), trisubstituted phenyl (2,3,4 or 2,3,5 or 2,3,6 or 3,4,5 or 3,4,6) or tetrasubstituted phenyl (2,3,4,5 or 2,3,5,6 or 2,4,5,6) or persubstituted phenyl or naphthyl, indenyl and any other kind of aromatic system with any substitution pattern, heteroaromatic systems with all kind of heteroatoms and substituents, directly attached carbonyl functionalities: R=COOH (acids), CO2R (esters), CONRR' (amides), C(O) (ketones) with R=H or different alkyl, substituted alkyl, aromatic groups and mixed versions, directly attached sulfonyl functionalities: R=SO3H (sulfonic acids), SO3R (sulfonic acid esters), SO2NRR' (sulfonamides), SO2R (sulfones) With R=H or different alkyl, substituted alkyl, aromatic groups and mixed versions; (b) heteroatoms: R=CN, F, Cl; R=OR, NRR' with R=H or different alkyl, substituted alkyl, aromatic groups and mixed versions
7. carboxylate salts (RCO2-) and carboxylic acids (RCO2H): where R is selected from the group consisting of: (a) C-atom-containing neighboring groups: H, methyl, ethyl, propyl, isopropyl, cyclopropyl, butyl, isobutyl, sec-butyl, tert-butyl, cyclobutyl, methylcyclopropyl, pentyl and isomers, hexyl and isomers, heptyl and isomers, octyl and isomers, nonyl and isomers, decyl and isomers, etc., alkynyl functionalities, benzyl with all kinds of substituted phenyl rings, alkyl groups containing the following functionalities: F, Cl, Br, CN, OH, C(O) (ketones), R—O—R (ethers), COOH (acids), C(O)OR (esters, lactones), C(O)NRR' (amides, lactames), SO3H (sulfonic acids), SO2OR (sulfonic acid esters), SO2NRR' (sulfonamides), R—SO2—R' (sulfones), NO2 (nitro-cpds.), phosphonic acid derivs., phosphorous acid derivs., phenyl, monosubstituted phenyl (2, 3, or 4), disubstituted phenyl (2,3 or 2,4 or 2,5 or 2,6 or 3,4 or 3,5), trisubstituted phenyl (2,3,4 or 2,3,5 or 2,3,6 or 3,4,5 or 3,4,6) or tetrasubstituted phenyl (2,3,4,5 or 2,3,5,6 or 2,4,5,6) or persubstituted phenyl or naphthyl, indenyl and any other kind of aromatic system with any substitution pattern, heteroaromatic systems with all kind of heteroatoms and substituents, directly attached carbonyl functionalities: R=COOH (acids), CO2R (esters), CONRR' (amides), C(O) (ketones) with R=H or different alkyl, substituted alkyl, aromatic groups and mixed versions, directly attached sulfonyl functionalities: R=SO3H (sulfonic acids), SO3R (sulfonic acid esters), SO2NRR' (sulfonamides), SO2R (sulfones) with R=H or different alkyl, substituted alkyl, aromatic groups and mixed versions;(b) heteroatoms: R=CN, F, Cl; R=OR, NRR' with R=H or different alkyl, substituted alkyl, aromatic groups and mixed versions.

Unsaturated Amides employable with the invention:
1) α,β-unsaturated amides with acyclic double bonds (FIG. 12; scheme B)
  A). Olefinic part (See FIG. 12, scheme B): i. R1=R2=R3=R4=H ; ii. R1=Z, R2=R3=R4=H; iii. R1=H, R2=Z, R3=R4=H; iv. R1=R2=H, R3=Z R4=H; Z=a carbon atom to which is attached one or more of the following groups: hydrogen, methyl, ethyl, propyl, isopropyl, cyclopropyl, butyl, isobutyl, sec-butyl, tert-butyl, cyclobutyl, methylcyclopropyl, pentyl and isomers, hexyl and isomers, heptyl and isomers, octyl and isomers, nonyl and isomers, decyl and isomers, etc., alkynyl functionalities, benzyl with phenyl rings of any substituents and of any substitution pattern, alkyl groups containing the following functionalities: F, Cl, Br, CN, OH, C(O) (ketones), R—O—R (ethers), C(O)OR (esters, lactones), C(O)NRR' (amides, lactams), SO2OR (sulfonic acid esters), SO2NRR' (sulfonamides), RSO2—R' (sulfones), NO2 (nitro-cpds.), phosphonic acid derivatives, phosphorous acid derivatives, phenyl, monosubstituted phenyl (2, 3, or 4), disubstituted phenyl (2,3 or 2,4 or 2,5 or 2,6 or 3,4 or 3,5), trisubstituted phenyl (2,3,4 or 2,3,5 or 2,3,6 or 3,4,5 or 3,4,6) or tetrasubstituted phenyl (2,3,4,5 or 2,3,5,6 or 2,4,5,6) or persubstituted phenyl or naphthyl, indenyl and any other kind of aromatic system with any substitution pattern, heteroaromatic systems with all kinds of heteroatoms and substituents, directly attached carbonyl functionalities: Z=CO2R (esters), CONRR' (amides), C(O) (ketones), directly attached sulfonyl functionalities: Z=SO3R (sulfonic acid esters), SO2NRR' (sulfonamides), SO2R (sulfones); Z can also be a heteroatom or pseudohalogen such as: CN, F, Cl, OR, NR'.
  B. Amide part: —CONR4R5 wherein i. R4=R5=H; ii. R4=Z, R5=H iii. R4=Z, R5=A or Z, wherein A=a. carbon atom to which is attached one or more of the following groups: hydrogen, methyl, ethyl, propyl, isopropyl, cyclopropyl, butyl, isobutyl, sec-butyl, tert-butyl, cyclobutyl, methylcyclopropyl, pentyl and isomers, hexyl and isomers, heptyl and isomers, octyl and isomers, nonyl and isomers, decyl and isomers, etc., alkynyl functionalities, benzyl with phenyl rings of any substituents and of any substitution pattern, alkyl groups containing the following functionalities: F, Cl, Br, CN, OH, C(O) (ketones), R—O—R (ethers), C(O)OR (esters, lactones), C(O)

NRR' (amides, lactams), SO2OR (sulfonic acid esters), SO2NRR' (sulfonamides), R—SO2—R' (sulfones), NO2 (nitro-cpds.), phosphonic acid derivatives, phosphorous acid derivatives, phenyl, monosubstituted phenyl (2, 3, or 4), disubstituted phenyl (2,3 or 2,4 or 2,5 or 2,6 or 3,4 or 3,5), trisubstituted phenyl (2,3,4 or 2,3,5 or 2,3,6 or 3,4,5 or 3,4,6) or tetrasubstituted phenyl (2,3,4,5 or 2,3,5,6 or 2,4,5,6) or persubstituted phenyl or naphthyl, indenyl and any other kind of aromatic system with any substitution pattern, heteroaromatic systems with all kinds of heteroatoms and substituents, directly attached carbonyl functionalities: Z, A=CO2R (esters), CONRR' (amides), C(O) (ketones), directly attached sulfonyl functionalities: Z, A=SO3R (sulfonic acid esters), SO2NRR' (sulfonamides), SO2R (sulfones); b) alternatively Z can also be a heteroatom such as: OR, NRR', where R=Z, R'=A (vide supra).

2) α,β-unsaturated amides with exocyclic double bonds (FIG. 12; scheme C) i. R1=H; ii. R1=A (defined below); Z=CH2 (2-azetidinone derivatives), C2H4 (2-pyrrolidinone derivatives), C3H6 (2-piperidinone derivatives), etc., substituted rings (C-branched, F, Cl, Br, CN, NO2 etc.), heteroatom-atom-containing rings with R—O—R' (ether), R—C(O)—R' (ketone), R—CO2—R' (lactone), R—CONRR'—R' (lactam), R—SO2—R' (sulfone);

A=a) carbon atom to which is attached one or more of the following groups: hydrogen, methyl, ethyl, propyl, isopropyl, cyclopropyl, butyl, isobutyl, sec-butyl, tert-butyl, cyclobutyl, methylcyclopropyl, pentyl and isomers, hexyl and isomers, heptyl and isomers, octyl and isomers, nonyl and isomers, decyl and isomers, etc., alkynyl functionalities, benzyl with phenyl rings of any substituents and of any substitution pattern, alkyl groups containing the following functionalities: F, Cl, Br, CN, OH, C(O) (ketones), R—O—R (ethers), C(O)OR (esters, lactones), C(O)NRR' (amides, lactams), SO2OR (sulfonic acid esters), SO2NRR' (sulfonamides), RSO2—R' (sulfones), NO2 (nitro-cpds.), phosphonic acid derivatives, phosphorous acid derivatives, phenyl, monosubstituted phenyl (2, 3, or 4), disubstituted phenyl (2,3 or 2,4 or 2,5 or 2,6 or 3,4 or 3,5), trisubstituted phenyl (2,3,4 or 2,3,5 or 2,3,6 or 3,4,5 or 3,4,6) or tetrasubstituted phenyl (2,3,4,5 or 2,3,5,6 or 2,4,5,6) or persubstituted phenyl or naphthyl, indenyl and any other kind of aromatic system with any substitution pattern, heteroaromatic systems with all kinds of heteroatoms and substituents, directly attached carbonyl functionalities: A CO2R (esters), CONRR' (amides), C(O) (ketones), directly attached sulfonyl functionalities: A=SO3R (sulfonic acid esters), SO2NRR' (sulfonamides), SO2R (sulfones); wherein A can also be a heteroatom such as: OR, NRR', wherein , R'=A (vide supra).

3. a,b-unsaturated amides with endocyclic double bonds (FIG. 12; scheme D) i. R1=H ii. R1=A or Z wherein Z=CH2 (2-pyrrolidinone derivatives), C2H4 (2-piperidinone derivatives), etc., substituted rings (C-branched, F, Cl, Br, CN, NO2 etc.), heteroatom-atom-containing rings with R—O—R' (ether), R—C(O)—R' (ketone), R—CO2—R' (lactone), R—CONRR'—R'' (lactam), RSO2—R' (sulfone)

wherein A a) carbon atom to which is attached one or more of the following groups: hydrogen, methyl, ethyl, propyl, isopropyl, cyclopropyl, butyl, isobutyl, sec-butyl, tert-butyl, cyclobutyl, methylcyclopropyl, pentyl and isomers, hexyl and isomers, heptyl and isomers, octyl and isomers, nonyl and isomers, decyl and isomers, etc., alkynyl functionalities, benzyl with phenyl rings of any substituents and of any substitution pattern, alkyl groups containing the following functionalities: F, Cl, Br, CN, OH, C(O) (ketones), R—OR (ethers), C(O)OR (esters, lactones), C(O)NRR' (amides, lactams), SO2OR (sulfonic acid esters), SO2NRR' (sulfonamides), R—SO2—R' (sulfones), NO2 (nitro-cpds.), phosphonic acid derivatives, phosphorous acid derivatives, phenyl, monosubstituted phenyl (2, 3, or 4), disubstituted phenyl (2,3 or 2,4 or 2,5 or 2,6 or 3,4 or 3,5), trisubstituted phenyl (2,3,4 or 2,3,5 or 2,3,6 or 3,4,5 or 3,4,6) or tetrasubstituted phenyl (2,3,4,5 or 2,3,5,6 or 2,4,5,6) or persubstituted phenyl or naphthyl, indenyl and any other kind of aromatic system with any substitution pattern, heteroaromatic systems with all kinds of heteroatoms and substituents, directly attached carbonyl functionalities: A=CO2R (esters), CONRR' (amides), C(O) (ketones), directly attached sulfonyl functionalities: A=SO3R (sulfonic acid esters), SO2NRR' (sulfonamides), SO2R (sulfones).

b) a heteroatom such as: OR, NRR', where R, R'=A (videsupra).

Substrate Scope-Chloramine Salts employable with the invention ($R^1SO_2NNaCl$ or $R^2OCONNaCl$)

wherein $R^1$=a) carbon atom to which is attached one or more of the following groups: hydrogen, methyl, ethyl, propyl, isopropyl, cyclopropyl, butyl, isobutyl, sec-butyl, tert-butyl, cyclobutyl, methylcyclopropyl, pentyl and isomers, hexyl and isomers, heptyl and isomers, octyl and isomers, nonyl and isomers, decyl and isomers, etc., alkynyl functionalities, benzyl with phenyl rings of any substituents and of any substitution pattern, alkyl groups containing the following functionalities: F, Cl, Br, CN, OH, C(O) (ketones), R—O—R (ethers), C(O)OR (esters, lactones), C(O)NRR' (amides, lactams), SO2OR (sulfonic acid esters), SO2NRR' (sulfonamides), R—SO2—R' (sulfones), NO2 (nitro-cpds.), phosphonic acid derivatives, phosphorous acid derivatives, phenyl, monosubstituted phenyl (2, 3, or 4), disubstituted phenyl (2,3 or 2,4 or 2,5 or 2,6 or 3,4 or 3,5), trisubstituted phenyl (2,3,4 or 2,3,5 or 2,3,6 or 3,4,5 or 3,4,6) or tetrasubstituted phenyl (2,3,4,5 or 2,3,5,6 or 2,4,5,6) or persubstituted phenyl or naphthyl, indenyl and any other kind of aromatic system with any substitution pattern, heteroaromatic systems with all kinds of heteroatoms and substituents.

b) heteroatom such as: OR, NRR', where R, R'=R1(vide supra).

wherein R2=a). carbon atom to which is attached one or more of the following groups: hydrogen, methyl, ethyl, propyl, isopropyl, cyclopropyl, butyl, isobutyl, sec-butyl, tert-butyl, cyclobutyl, methylcyclopropyl, pentyl and isomers, hexyl and isomers, heptyl and isomers, octyl and isomers, nonyl and isomers, decyl and isomers, etc., alkynyl functionalities, benzyl with phenyl rings of any substituents and of any substitution pattern, alkyl groups containing the following functionalities: F, Cl, Br, CN, OH, C(O) (ketones), R—O—R (ethers), C(O)OR (esters, lactones), C(O)NRR' (amides, lactams), SO2OR (sulfonic acid esters), SO2NRR' (sulfonamides), R—SO2—R' (sulfones), NO2 (nitro-cpds.), phosphonic acid derivatives, phosphorous acid derivatives, phenyl, monosubstituted phenyl (2, 3, or 4), disubstituted phenyl (2,3 or 2,4 or 2,5 or 2,6 or 3,4 or 3,5), trisubstituted phenyl (2,3,4 or 2,3,5 or 2,3,6 or 3,4,5 or 3,4,6) or tetrasubstituted phenyl (2,3,4,5 or 2,3,5,6 or 2,4,5,6) or persubstituted phenyl or naphthyl, indenyl and any other kind of aromatic system with any substitution pattern, heteroaromatic systems with all kinds of heteroatoms and substituents.

Suitable Solvents and Solvent Mixtures employable with the invention: Any volume to volume mixture of water and the folowing solvents (i.e pure water to 0:1 water:solvent):

1. alcohols: methanol, ethanol, n-propanol, i-propanol, n-butanol, i-butanol, sec-butanol, t-butanol, ethylene glycol, glycerol, and the like.
2. ethers: tetrahydrofuran
3. ketones: acetone, methyl ethyl ketone
4. nitrites: acetonitrile.

Figure 14A:
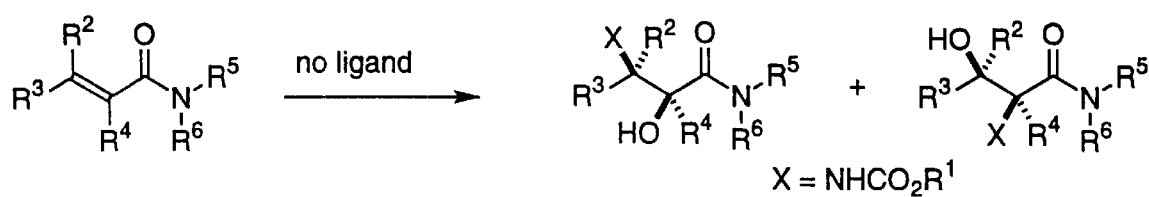
FIG. 14 illustrates A) AA process on acyclic α,β unsaturated amide without a ligand to form racemic products and equal distribution of regioisomers; B) AA process on acyclic α,β unsaturated amide with a ligand to form nonracemic products and weighted distribution of regioisomers; C) shows general deprotection of sulfonamides using standard conditions known in the art and suggested in the synthetic protocals.
Figure 14B:
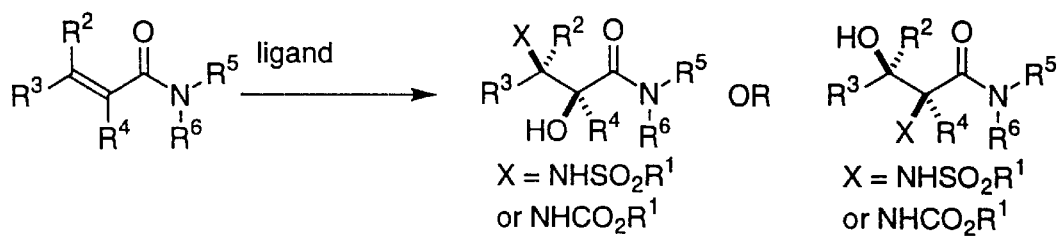
Figure 14C:
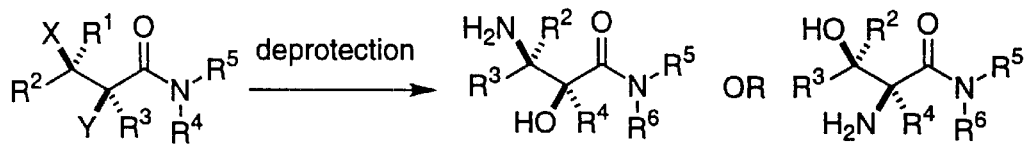
Figure 15:
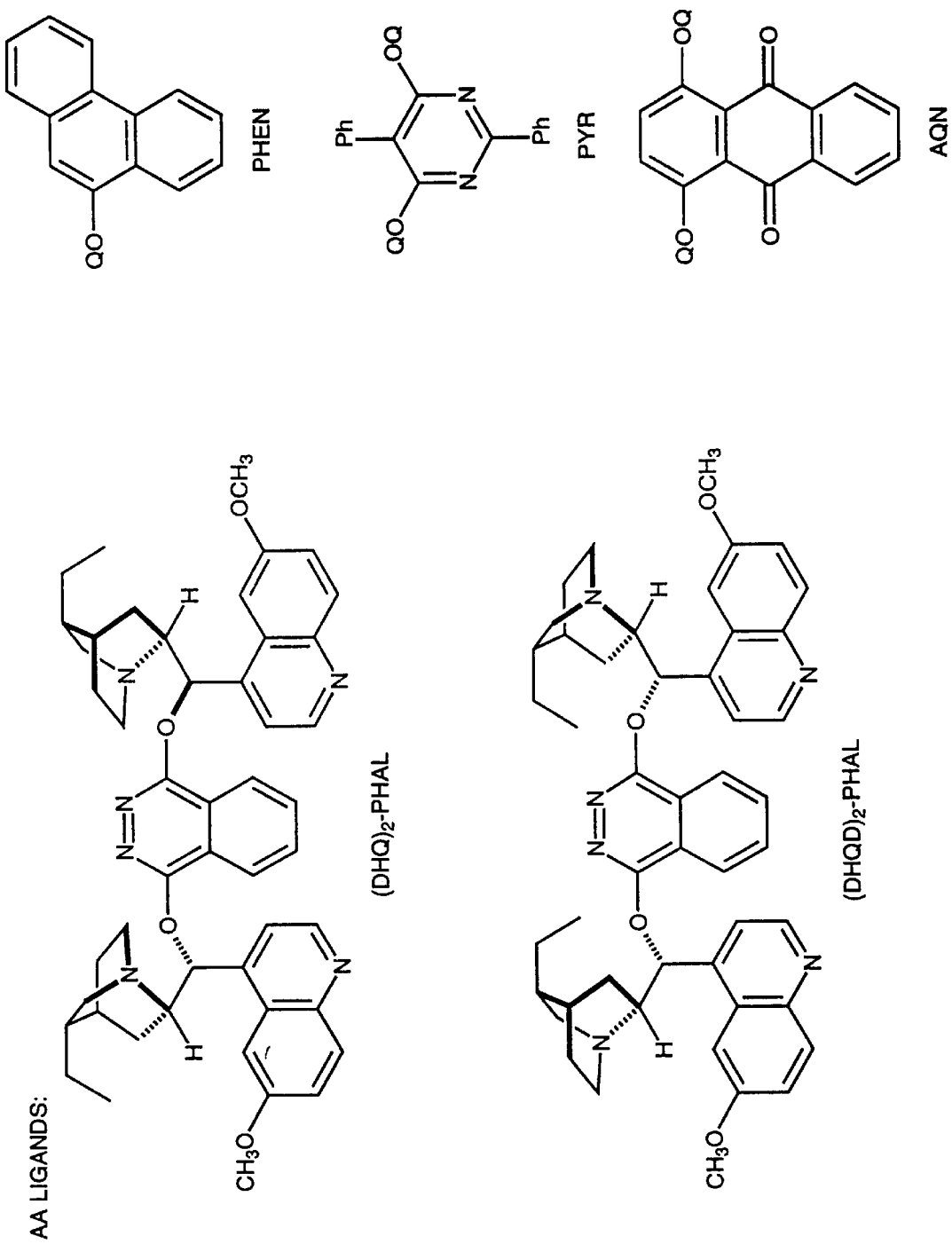
FIG. 15 shows commercially available and suggested ligands for the AA process.
Figure 16:
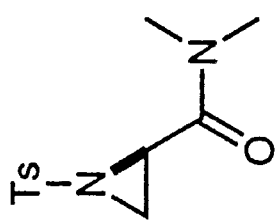
FIG. 16 shows various aziridines and suggests effective nucleophiles for regioselective ring opening.
Figure 16:
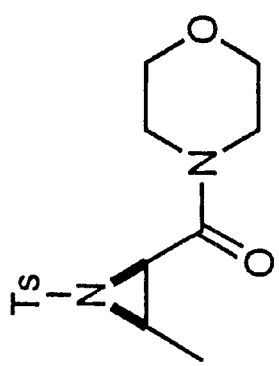
Figure 16:
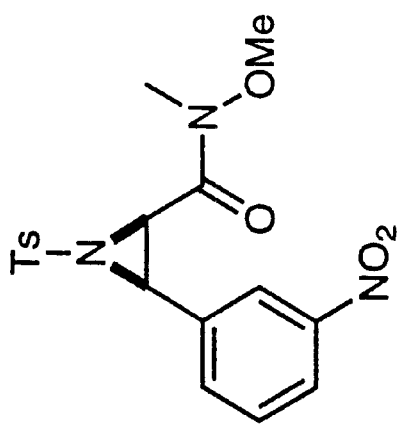
Figure 16:
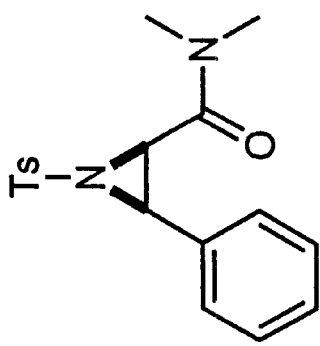
Figure 20:
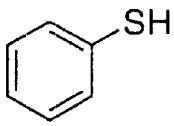
FIG. 20 illustrates various reactions run with compounds 4b, 4g, 4j and 4i with thiol nucleophiles using the following conditions: a) Reaction was run in neat amine (ca. 10 equiv.), 80° C.; b) Reaction was run in n-PrOH (1 M), 80° C.; c) Reaction was run in DMF (1 M), 80° C.; d) Recrystalized yields in parentheses.
Figure 20:
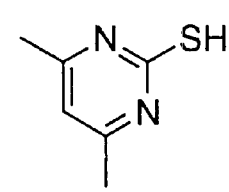
Figure 22:
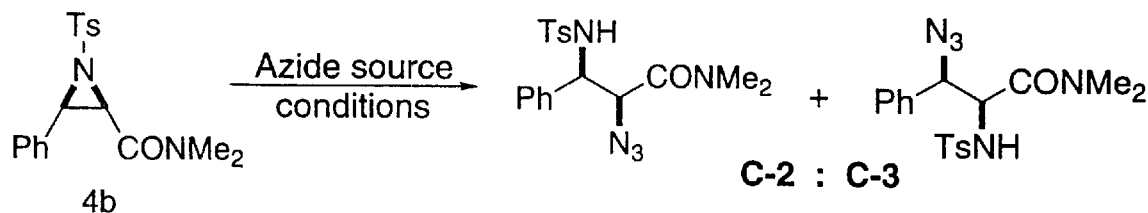
FIG. 22 illustrates various azide regioselectivity studies with aziridine 4b using the following conditions: a) Reaction run at 70° C.; b) Reaction run at reflux; c) Recrystalized yield in parentheses.
Figure 24A:
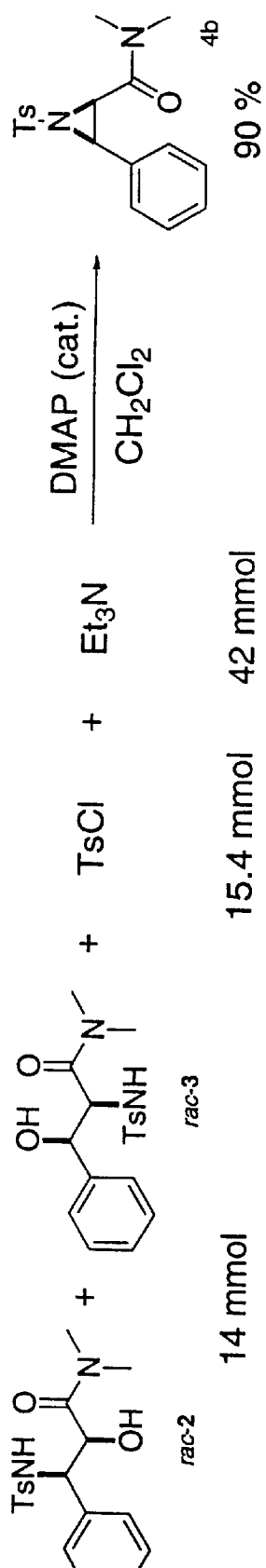
FIG. 24 illustrates a) conversion of the regioisomeric hydroxysulfonamides to a single compound; b) the nucleophilic opening of the aziridine.
Figure 24B:
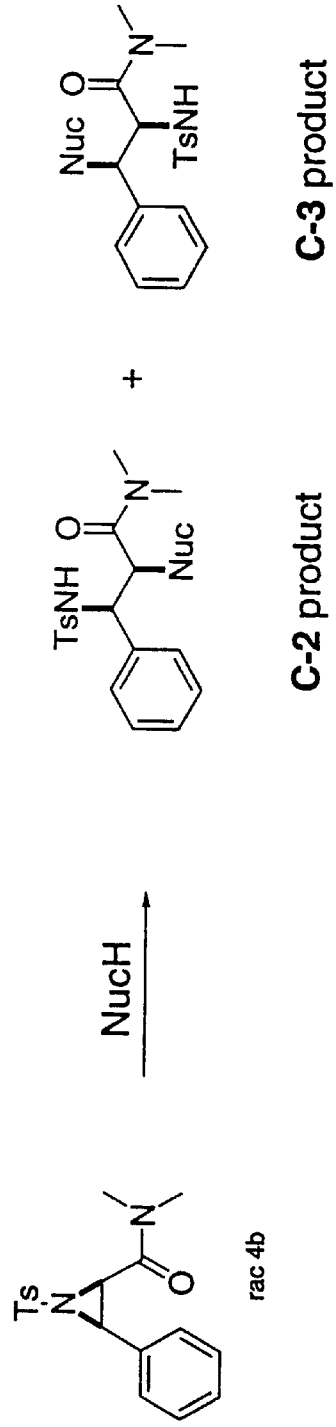
Figure 25:
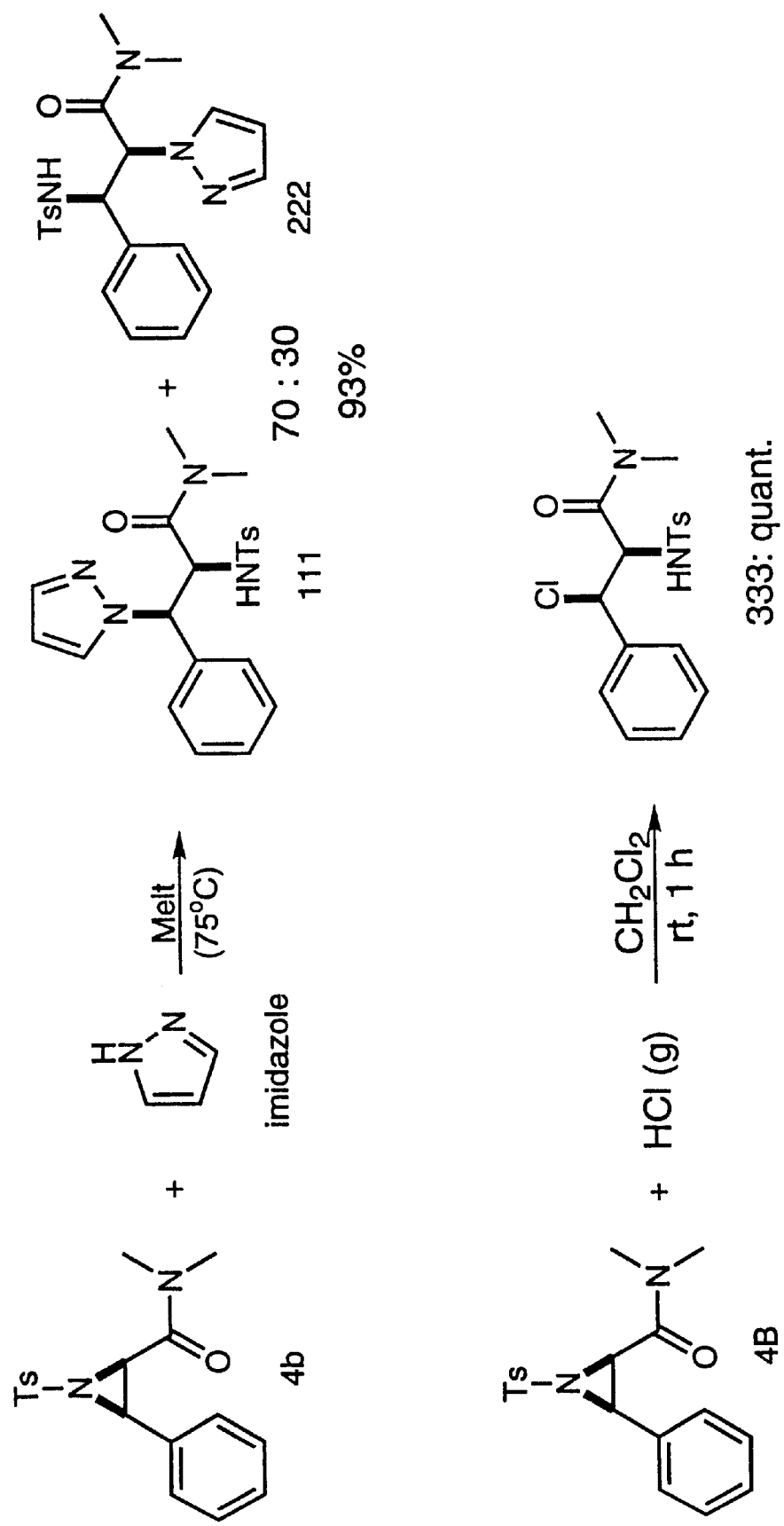
FIG. 25 illustrates additional aziridines openings using imidazole at 75° C. (otherwise using general conditions) and bubbling HCl gas in a methylene chloride solution at room temperature for 1 hour (otherwise using general conditions) to form 111, 222, and 333.
Figure 26A:
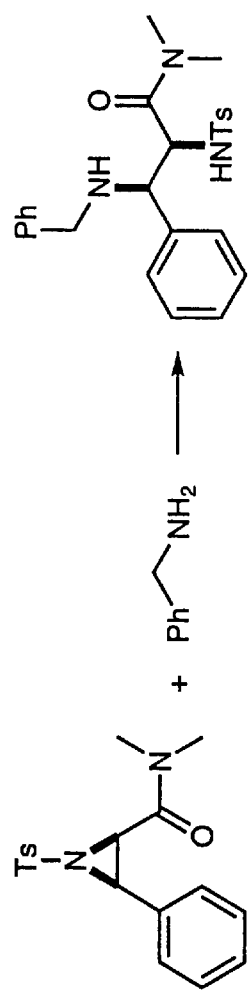
FIG. 26 illustrates various regioselective routes to α-amino sulfonamides: a) via direct amine addition; b) via sulfonamide addition followed by alkylation and deprotection.
Figure 26B:
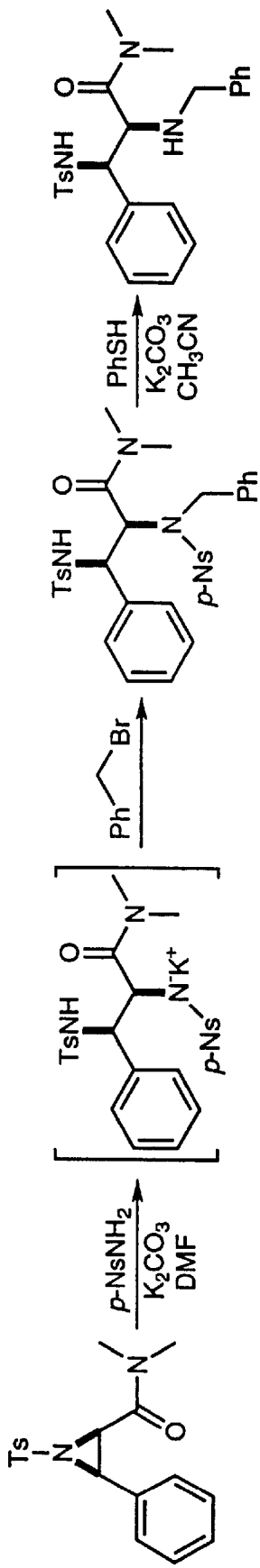
Figure 27:
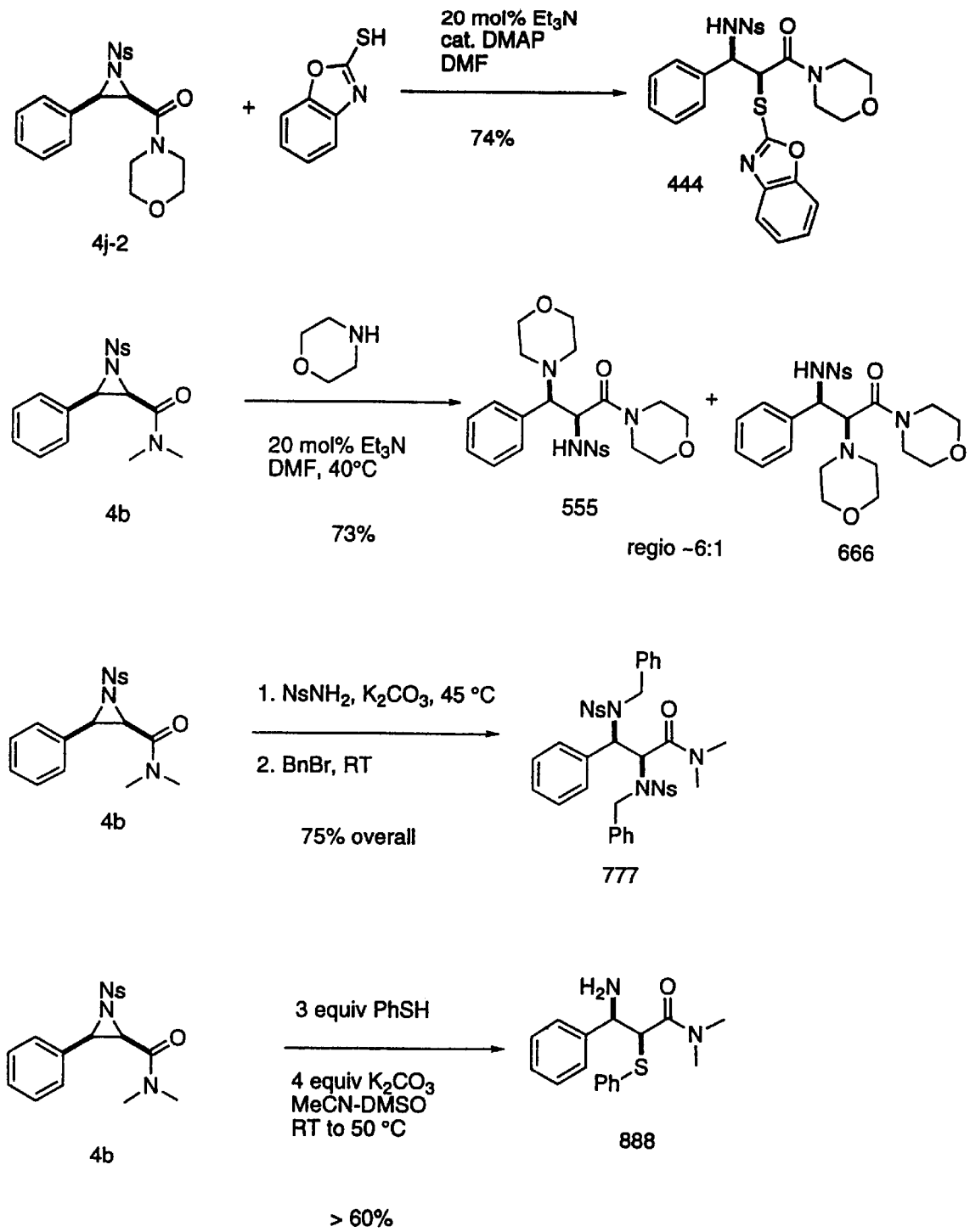
FIG. 27 illustrates additional aziridines openings using various thiols and amines.
Figure 28:
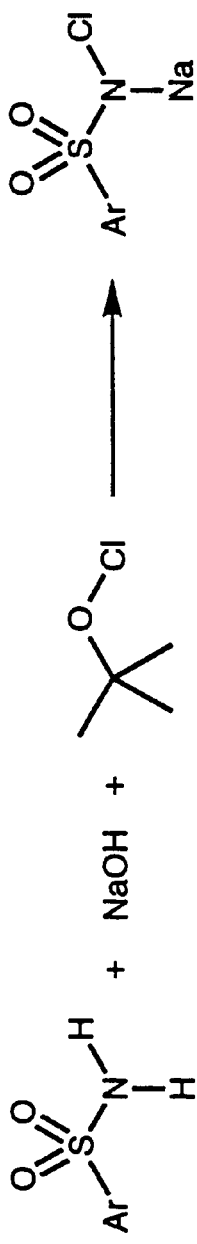
FIG. 28 shows chloramine generation and a typical reaction scheme for the aminohydroxylation reaction.
Figure 28:
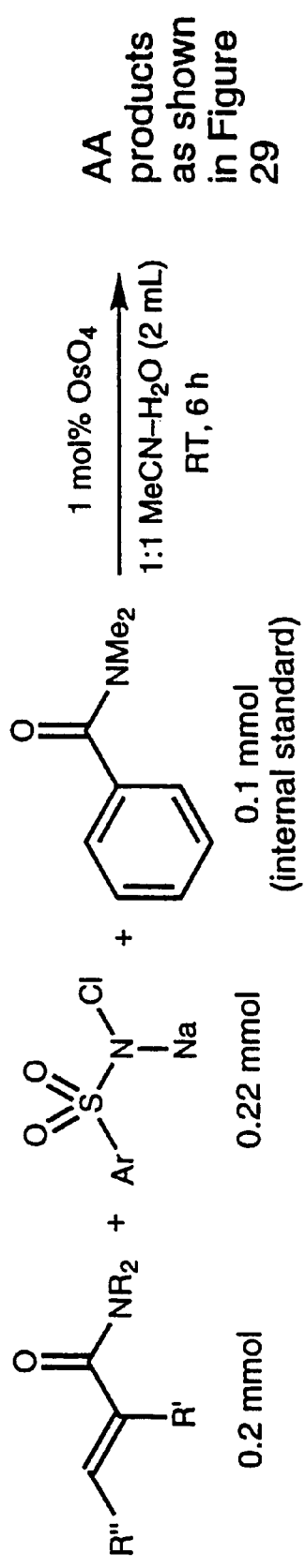

General experimental procedure for the aminohydroxylation of α,β-unsaturated amides for cases in which the products are insoluble in the reaction solution-described for a 1 mmol (1 mol) scale reaction (FIG. 14, schemes A and B). Procedure: To a stirred solution of the α,β-unsaturated amide [1 mmol (1 mol), see above for a list of suitable olefins] and a chloramine salt [1.25 mmol (1.25 mol), see above for a list of suitable sulfonamide-based and carbamate-based chloramine salts] in a 1:1 [v:v] mixture of t-BuOH and water (2 mL (2 L), see above for a list of solvents compatible with this system] is added K2OSO2(OH)4 [0.92 mg, 2.5 mmol (0.92 g, 2.5 mmol), 0.25 mol %] in one portion at room temperature. The reaction mixture is stirred at RT until tlc indicates that the starting α,β-unsaturated amide has disappeared. Workup: Water [1 mL (1 L)] is added and the slurry is cooled in an ice/water bath until the temperature of the reation is ca., 5° C. The solid product is collected by filtration, washed with water [2×1 mL (2×1 L)], and dried under a stream of air to afford the mixture of hydroxysulfonamides or hydroxycarbamate regioisomers. Yield: 88–95%.

General experimental procedure for the aminohydroxylation of α,β-unsaturated amides for cases in which the products are soluble in the reaction solution-described for a 1 mmol (1 mol) scale reaction (FIG. 14, scheme A). Procedure: The same procedure as in the above case is used with the exception that 1.0 equivalent of the chloramine salt and 0.50 mol % of the osmium catalyst are used. Workup: Na$_2$SO$_3$ [0.20 g (200 g)] and ethyl acetate [1 mL (1 L)] are added and the slurry is stirred for 1 h. The phases are separated and the aqueous phase is washed with ethyl acetate until no product remains in the aqueous layer [usually 2×1 mL (2×1 L)]. The combined organic phases are shaken with brine [1 mL (1 L)], dried over MgSO$_4$ or Na$_2$SO$_4$ and evaporated to afford the mixture of hydroxysulfonamides or hydroxycarbamate regioisomers. Yield: 90–99%.

General experimental procedure for the aminohydroxylation of α,β unsaturated amides in the presence of chiral ligands (FIG. 14, scheme B): Procedure: To a stirred solution of the α,β-unsaturated amide [1 equivalent, see above for a list of suitable olefins], a chiral ligand [0.001–1.0 equivalents, see above for a list of suitable chiral alkaloid ligands] and a chloramine salt [1.0–5.0 equivalents, see above for a list of suitable sulfonamide-based and carbamate-based chloramine salts] in a suitable organic solvent-water mixture [see above for a list of solvents compatible with this system] is added K$_2$OSO$_2$(OH)$_4$ [0.0001–0.10 equivalents] in one portion at room temperature. The reaction mixture is stirred until tlc indicates that the starting α,β unsaturated amide has disappeared. Workup: Same as for the above cases in the absence of ligand.

Removal of the sulfonamide groups from the hydroxysulfonamides to afford free aminoalcohols (FIG. 14, scheme C): The sulfonamide groups in the hydroxysulfonamides can be removed using procedures well known in the art including the following reagents: acids (e.g. HBr/HOAc, trimethylsilyl iodide, HI, electrochemical reduction, samarium(II) iodide, thiols, dissolving metal reduction (e.g. Na/ammonia), etc. to afford the free aminoalcohols. The carbamate groups in the hydroxycarbamates can be removed using the following reagents: acids (e.g. aqueous HCl, trimethylsilyl iodide, HBr/HOAc, trifluoroacetic acid, etc, bases (e.g. KOH, piperidine, etc.), hydrogenolysis, etc.

What is claimed:

1. A method for converting an α,β-saturated amide substrate to a blocked or unblocked α,β-substituted amino amide product, the blocked α,β-substituted amino amide product having a blocked amino group, the method comprising the following steps:

Step 1) Oxidizing the α,β-unsaturated amide substrate with a nitrogen source for making a racemic mixture of an α,β-hydroxy-amino amide intermediate having a blocked amino group; then Step 2) Cyclodehydrating the α,β-hydroxy-amino amide intermediate described in step 1 for producing an α,β-N-blocked-aziridine amide intermediate having an aziridine ring; then Step 3) Opening the aziridine ring of the α,β-N-blocked-aziridine amide intermediate described in step 2 with a nucleophile in a regioselective manner for making the blocked α,β-substituted amino amide product; and then p1 Step 4) Optionally deblocking the amino group of the blocked α,β-substituted amino amide product to produce the unblocked α,β-substituted amino amide product.

2. The method described in claim 1 wherein, in said Step 1, the oxidation being a regioselective osmium-catalyzed aminohydroxylation.

3. The method described in claim 1 wherein, in said Step 1, the nitrogen source is selected from a group consisting of carbamate and sulfonamide.

4. The method described in claim 1 wherein, in said Step 3, the nucleophile is a hydrocarbon having a nucleophilic moiety selected from a group consisting of thiol, alcohol, nitrile and amine.

5. The method described in claim 1 further comprising the following step:

Step 5) Hydrolyzing the amide group of the blocked or unblocked α,β-substituted amino amide product for forming a blocked or unblocked α,β-substituted β-amino acid.

6. A method for converting an α-β unsaturated amide substrate to a racemic mixture of an α-hydroxy-β-amino regio-isomer amide product having a blocked amino group, said method comprising the following step:

Step 1: Admixing a nitrogen source and a hydroxyl radical with the α-β unsaturated amide substrate for forming the α-hydroxy-β-amino regio-isomer amide product, the method being of a type which employs a reaction solution which includes osmium as a catalyst, the α-β unsaturated amide substrate being present and soluble at a stoichiometric concentration within the reaction solution, the osmium being present and soluble within the reaction solution at a catalytic concentration, said nitrogen source being selected from a group consisting of sulfonamide and carbamate.

7. A method for converting an α-β unsaturated amide substrate to an asymmetric α-hydroxy-β-amino regio-isomer amide product having a blocked amino group, said method comprising the following step:

Step 1: Admixing a nitrogen source, a chiral ligand, and a hydroxyl radical with the α-β unsaturated amide substrate for enantiomerically directing the addition of the nitrogen source and hydroxyl radical for forming the asymmetric α-hydroxy-β-amino regio-isomer amide product, the method being of a type which employs a reaction solution which includes osmium as a catalyst, the α-β unsaturated amide substrate being present and soluble at a stoichiometric concentration within the reaction solution, the osmium being present and soluble within the reaction solution at a catalytic concentration, said nitrogen source being selected from the group consisting of sulfonamide and carbamate.

8. A method as described in claim 7 wherein admixing occurs in a co-solvent mixture containing an organic component and an aqueous component.

9. A method for converting an α,β-unsaturated ester substrate to a blocked or unblocked α,β-substituted amino ester product, the blocked α,β-substituted amino ester product having a blocked amino group, the method comprising the following steps:

Step 1) Oxidizing the α,β-unsaturated ester substrate with a nitrogen source for making a racemic mixture of an α,β-hydroxy-amino ester intermediate having a blocked amino group; then Step 2) Cyclodehydrating the α,β-hydroxy-amino ester intermediate described in step 1 for producing an α,β-N-blocked-aziridine ester intermediate having an aziridine ring; then Step 3) Opening the aziridine ring of the α,β-N-blocked-aziridine ester intermediate described in step 2 with a nucleophile in a regioselective manner for making the blocked α,β-substituted amino ester product; and then Step 4) Optionally deblocking the amino group of the blocked α,β-substituted amino ester product to produce the unblocked α,β-substituted amino ester product.

10. The method described in claim 9 wherein, in said Step 1, the oxidation being a regioselective osmium-catalyzed aminohydroxylation.

11. The method described in claim 9 wherein, in said Step 1, the nitrogen source is selected from a group consisting of carbamate and sulfonamide.

12. The method described in claim 9 wherein, in said Step 3, the nucleophile is a hydrocarbon having a nucleophilic moiety selected from a group consisting of thiol, alcohol, nitrile and amine.

13. The method described in claim 9 further comprising the following step: Step 5) Hydrolyzing the ester group of the blocked or unblocked α,β-substituted amino ester product for forming a blocked or unblocked α-substituted β-amino acid.

* * * * *